(12) United States Patent
Modelska et al.

(10) Patent No.: US 9,631,013 B2
(45) Date of Patent: Apr. 25, 2017

(54) THERAPEUTIC METHOD FOR PANCREATIC CANCER

(71) Applicant: FibroGen, Inc., San Francisco, CA (US)

(72) Inventors: Katharina Modelska, Millbrae, CA (US); Frank Valone, Mill Valley, CA (US); Vincent Picozzi, Mercer-Island, WA (US); Wen Shi, San Francisco, CA (US)

(73) Assignee: FIBROGEN, INC., San Francisco, CA (US)

( * ) Notice: Subject to any disclaimer, the term of this patent is extended or adjusted under 35 U.S.C. 154(b) by 0 days.

(21) Appl. No.: 14/593,819

(22) Filed: Jan. 9, 2015

(65) Prior Publication Data

US 2015/0210760 A1   Jul. 30, 2015

Related U.S. Application Data

(60) Provisional application No. 61/932,316, filed on Jan. 28, 2014.

(51) Int. Cl.

| | |
|---|---|
| *A61K 39/395* | (2006.01) |
| *C07K 16/22* | (2006.01) |
| *A61K 31/713* | (2006.01) |
| *A61K 45/06* | (2006.01) |
| *A61K 31/7068* | (2006.01) |
| *A61K 31/337* | (2006.01) |
| *A61K 47/48* | (2006.01) |
| *A61B 10/04* | (2006.01) |
| *C12N 15/113* | (2010.01) |
| *A61K 39/00* | (2006.01) |
| *A61N 5/10* | (2006.01) |

(52) U.S. Cl.
CPC .............. *C07K 16/22* (2013.01); *A61B 10/04* (2013.01); *A61K 31/337* (2013.01); *A61K 31/7068* (2013.01); *A61K 31/713* (2013.01); *A61K 39/3955* (2013.01); *A61K 45/06* (2013.01); *A61K 47/48284* (2013.01); *A61K 47/48884* (2013.01); *C12N 15/1136* (2013.01); *A61K 2039/505* (2013.01); *A61K 2039/54* (2013.01); *A61K 2039/545* (2013.01); *A61N 2005/1098* (2013.01); *C07K 2317/76* (2013.01); *C12N 2310/11* (2013.01); *C12N 2310/14* (2013.01); *C12N 2310/141* (2013.01); *C12N 2310/531* (2013.01)

(58) Field of Classification Search
None
See application file for complete search history.

(56) References Cited

U.S. PATENT DOCUMENTS

| | | | |
|---|---|---|---|
| 5,770,209 A | 6/1998 | Grotendorst et al. | |
| 6,492,129 B1 | 12/2002 | Grotendorst | |
| 7,115,390 B1 | 10/2006 | Grotendorst et al. | |
| 8,865,173 B2 | 10/2014 | Spong et al. | |
| 9,102,721 B2 | 8/2015 | Neff et al. | |
| 2003/0113816 A1 | 6/2003 | Weitz et al. | |
| 2004/0248206 A1 | 12/2004 | Lin et al. | |
| 2014/0127224 A1 | 5/2014 | Neff et al. | |

FOREIGN PATENT DOCUMENTS

| | | |
|---|---|---|
| EP | 1043335 | 10/2000 |
| WO | WO 2010/119991 A2 | 10/2010 |
| WO | WO 2012/100262 | * 7/2012 |

OTHER PUBLICATIONS

Quiros et al., Cancer Investigation, 25(4):267-273, 2007, DOI: 10.1080/07357900701206356.*
Moss et al., OncoTargets and Therapy,3:111-127, 2010.*
Kim et al., Journal of Gastrointestinal Surgery, 6(5):763-769, 2002.*
Katz et al., Cancer, 118:5749-56, 2012.*
Cascinu et al., Annals of Oncology 21 (Supplement 5): v55-v58, 2010.*
Von Hoff et al., NEJM, 369(18):1691-1703, Oct. 2013.*
Gillen et al., (2010) Preoperative/Neoadjuvant Therapy in Pancreatic Cancer: A Systematic Review and Meta-analysis of Response and Resection Percentages. PLoS Med 7(4): e1000267. doi:10. 1371/journal.pmed.1000267.*
Adler SG: "Phase 1 study of anti-CTGF monoclonal antibody in patients with diabetes and microalbuminuria." Clin J Am Soc Nephrol. Aug. 2010:5(8):1420-8.
Aikawa T: "Connective tissue growth factor-specific antibody attenuates tumor growth, metastasis and angiogenesis in an orthotopic mouse model of pancreatic cancer." Mol Cancer Ther, May 2006: 5(5):1108-16.
Bennewith KL: "The Role of Tumor Cell-Derived Connective Tissue Growth Factor (CTGF/CCN2) in Pancreatic Tumor Growth." Cancer Res. Feb. 1, 2009;69(3):775-84.
Dornhofer N: "Connective tissue growth factor-specific monoclonal antibody therapy inhibits pancreatic tumor growth and metastasis." Cancer Res, Jun. 2006: 66(11):5816-27.
Karger A: "Molecular insights into connective tissue growth factor action in rat pancreatic stellate cells." Cell Signal. Oct. 2008;20(10):1865-72.
Kwon S: "Expression of connective tissue growth factor in pancreatic cancer cell lines." Int J Oncol. Oct. 2007;31(4):693-703.
Lieber M: Establishment of a continuous tumor-cell line (panc-1) from a human carcinoma of the exocrine pancreas. Int J Cancer. May 15, 1975;15(5):741-7.
Wenger C: Expression and differential regulation of connective tissue growth factor in pancreatic cancer cells. Oncogene, Jan. 28, 1999;18(4)1073-80.
Neesse A: CTGF antagonism with mAb FG-3019 enhances chemotherapy response without increasing drug delivery in murine ductal pancreas cancer. PNAS. Jul. 23, 2013; 110(30) 12325-12330.

* cited by examiner

*Primary Examiner* — Marianne P Allen
(74) *Attorney, Agent, or Firm* — FibroGen, Inc.; Leanne C. Price; Paul Burchardt

(57) ABSTRACT

The present invention relates to methods and medicaments useful for treating locally advanced pancreatic cancer (LAPC). Improved therapeutic methods and regimens comprising anti-connective tissue growth factor (CTGF) agents, including anti-CTGF antibodies, are provided. Included are induction therapies for converting unreseetable LAPC into borderline or resectable status.

6 Claims, 2 Drawing Sheets

THERAPEUTIC METHOD FOR PANCREATIC CANCER

This application claims the benefit of U.S. Provisional Application Ser. No. 61/932,316 filed on 28 Jan. 2014, incorporated in its entirety by reference herein.

FIELD OF THE INVENTION

The present invention relates to methods useful for treating pancreatic cancer (PC), particularly locally advanced pancreatic cancer (LAPC). Improved therapeutic methods and regimens comprising anti-connective tissue growth factor (CTGF) agents, including anti-CTGF antibodies, are provided.

BACKGROUND OF THE INVENTION

Pancreatic cancer has one of the worst prognosis with a 5 year overall survival (OS) rate of 6% (Hosein P et al. *BMC Cancer* 2012, 12:199). In general, curative therapy is only achieved through surgery where all gross disease is resected and surgical margins are microscopically free of disease (R0). Unfortunately, only about 10-20% of patients are candidates for surgery at diagnosis, i.e., have resectable LAPC. A further 30-40% of newly diagnosed patients present with LAPC, but are not candidates for surgery because vascular encasement by tumor renders the disease unresectable.

In an effort to increase the overall survival rate, induction therapy has been under investigation at multiple centers to "downstage," LAPC, i.e., convert unresectable tumors into at least borderline resectable status, thereby making LAPC patients candidates for surgery. A recent literature review demonstrates that induction therapy has about a 33% success rate in downstaging eligible LAPC patients (Gillen S, et al. *PLoS Med* 2010 7(4):e1000267). Successfully downstaged LAPC patients that undergo tumor resection that achieves R0 margins have similar survival rates to LAPC patients that present with resectable disease.

Further improvements in induction therapies are required to increase the percentage of LAPC patients that are elible for tumor resection. Induction therapies comprising an anti-CTGF agent can address this pressing medical need.

SUMMARY OF THE INVENTION

The present invention provides for improved methods and therapeutic regimens for treating pancreatic cancer. In one aspect of the invention, a method is provided for treating unresectable LAPC in a subject, the method comprises administering to the subject an effective amount of an induction therapy comprising an anti-CTGF agent, and resecting the LAPC, if following the administration of the induction therapy, the LAPC becomes resectable or borderline resectable, thereby treating the subject.

In some embodiments, the anti-CTGF agent is an anti-CTGF antibody, anti-CTGF antibody fragment, anti-CTGF antibody mimetic or anti-CTGF oligonucleotide. In specific embodiments, the anti-CTGF agent is an anti-CTGF antibody. In other embodiments, the anti-CTGF antibody is identical to CLN-1. In additional embodiments, the anti-CTGF antibody binds to the same epitope recognized by CLN-1. In further embodiments, the anti-CTGF oligonucleotide is an antisense oligonucleotide, siRNA, shRNA or miRNA.

In some embodiments, the induction therapy comprises a chemotherapy agent. In further embodiments, the chemotherapy agent is selected from the group consisting of antimetabolites, mitotic inhibitors, topisomerase inhibitors, alkylating agents, anti-tumor antibiotics, differentiating agents and hormones.

In some embodiments, the chemotherapy agent is an antimetabolite. In further embodiments, the antimetabolite is selected from the group consisting of a folate analogue, a purine analogue, a pyrimidine analogue and a ribonucleotide reductase inhibitor. In other embodiments, the pyrimidine analogue is gemcitabine. In additional embodiments, gemcitabine is administered at a dose of about 1000 mg/m$^2$.

In some embodiments, the chemotherapy agent is a mitotic inhibitor. In other embodiments, the mitotic inhibitor is selected from the group consisting of docetaxel, paclitaxel, nab-paclitaxel, vinblastine, vinorelbine, vincristine and vindesine. In further embodiments, the mitotic inhibitor is paclitaxel. In specific embodiments, paclitaxel is nanoparticle size. In additional embodiments, the nanoparticle size paclitaxel is bound to a carrier. In further embodiments, the carrier is albumin. In certain embodiments, the mitotic inhibitor is nab-paclitaxel. In particular embodiments, nab-paclitaxel is administered at a dose of about 125 mg/m$^2$.

In some embodiments, the LAPC is an adenocarcinoma. In further embodiments, the adenocarcinoma is ductal adenocarcinoma.

In some embodiments, the method further comprises laparoscopic staging. In additional embodiments, laparoscopic staging is performed prior to administering the induction therapy. In other embodiments, laparoscopic staging is performed after administering the induction therapy.

In other embodiments, the method further comprises requiring, following completion of induction therapy, at least a 50% reduction in a tumor marker level compared to a baseline measurement, prior to resecting the LAPC.

In additional embodiments, the method further comprises requiring, following completion of induction therapy, at least a 30% reduction in FDG-PET SLIV$_{max}$ compared to a baseline measurement, prior to resecting the LAPC.

In another aspect of the invention, a method is provided for treating a subject with pancreatic cancer, the method comprises administering to the subject an effective amount of an induction therapy comprising an anti-CTGF agent and a mitotic inhibitor, thereby treating the subject. In some embodiments, the subject has advanced pancreatic cancer. In additional embodiments, method further comprises resecting the pancreatic cancer.

In some embodiments, treating a subject an effective amount of an induction therapy comprising an anti-CTGF agent and a mitotic inhibitor increases the subject's survival. In further embodiments, the increase in survival is disease-free survival or overall survival. In other embodiments, disease-free survival is increased at least 1 month beyond historical controls. In additional embodiments, overall survival is increased at least 1 month beyond historical controls.

In some embodiments, the increase in survival is an increase in time to tumor progression. In further embodiments, time to tumor progression is increased at least 1 month beyond historical controls.

These and other embodiments of the present invention will readily occur to those of skill in the art in light of the disclosure herein, and all such embodiments are specifically contemplated.

Each of the limitations of the invention can encompass various embodiments of the invention. It is, therefore, anticipated that each of the limitations of the invention involving any one element or combinations of elements can be included in each aspect of the invention. This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting.

DESCRIPTION OF THE INVENTION

Figure 1:
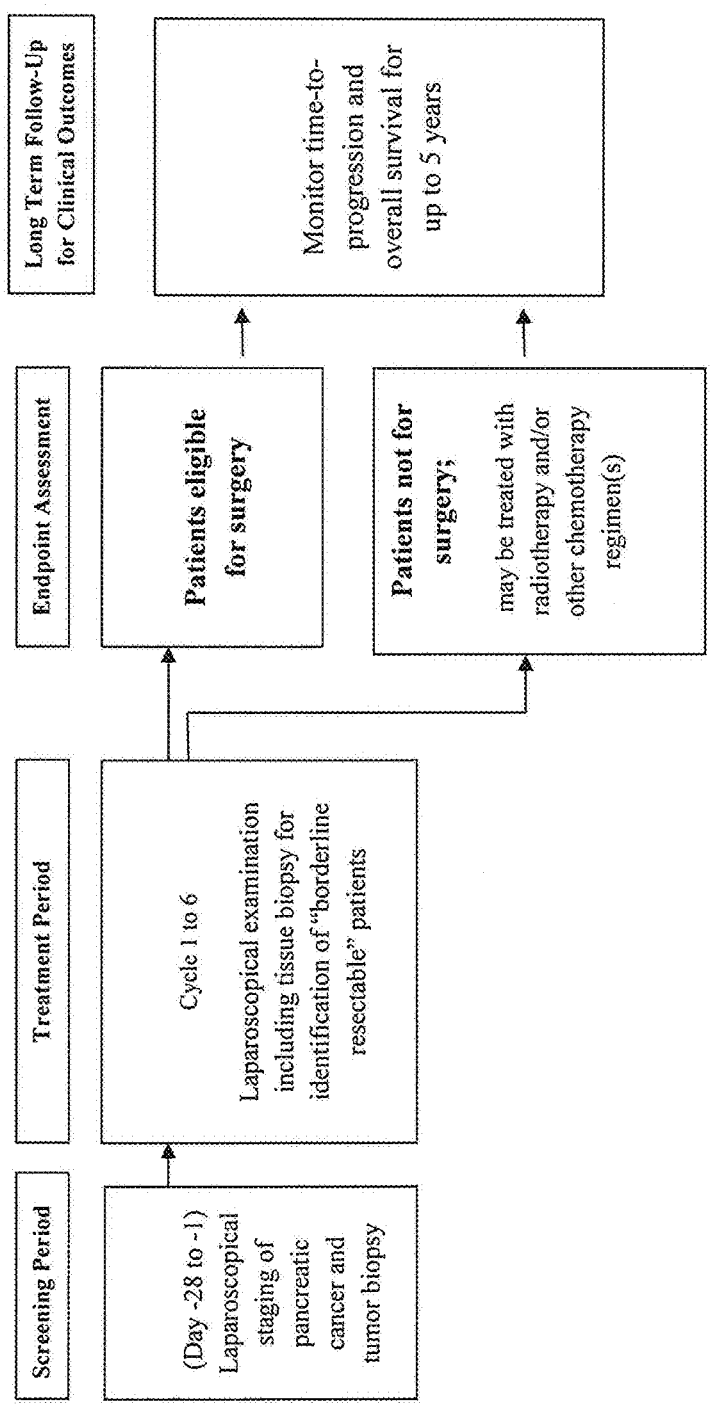
FIG. 1 is a schematic overview of the study design for a Phase 1, open-label study evaluating the rate of R0 resection after induction therapy with gemcitabine, nab-paclitaxel and the anti-CTGF antibody, FG-3019, in subjects with unresectable LAPC.

Before the present compositions and methods are described, it is to be understood that the invention is not limited to the particular methodologies, protocols, cell lines, assays, and reagents described, as these may vary. It is also to be understood that the terminology used herein is intended to describe particular embodiments of the present invention, and is in no way intended to limit the scope of the present invention as set forth in the appended claims.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications cited herein are incorporated herein by reference in their entirety for the purpose of describing and disclosing the methodologies, reagents, and tools reported in the publications that might be used in connection with the invention. Nothing herein is to be construed as an admission that the invention is not entitled to antedate such disclosure by virtue of prior invention.

The practice of the present invention will employ, unless otherwise indicated, conventional methods of chemistry, biochemistry, molecular biology, cell biology, genetics, immunology and pharmacology, within the skill of the art. Such techniques are explained fully in the literature. See, e.g., Gennaro, A. R., ed. (1990) *Remington Pharmaceutical Sciences*, 18th ed., Mack Publishing Co.; Hardman, J. G., Limbird, L. E., and Gilman, A. G., eds. (2001) *The Pharmacological Basis of Therapeutics*, 10th ed., McGraw-Hill Co.; Colowick. S. et al., eds., *Methods In Enzymology*, Academic Press, Inc.; Weir, D. M., and Blackwell, C. C., eds, (1986) *Handbook of Experimental Immunology*, Vols. 1-IV, Blackwell Scientific Publications; Maniatis, T. et al., eds. (1989) *Molecular Cloning: A Laboratory Manual*, 2nd edition, Vols. I-III, Cold Spring Harbor Laboratory Press; Ausubel, F. M. et al., eds. (1999) *Short Protocols in Molecular Biology*, 4th edition, John Wiley & Sons; Ream et al., eds. (1998) *Molecular Biology Techniques: An Intensive Laboratory Course*, Academic Press; Newton, C. R., and Graham, A., eds, (1997) *PCR (Introduction to Biotechniques Series)*, 2nd ed., Springer Verlag.

The section headings are used herein for organizational purposes only, and are not to be construed as in any way limiting the subject matter described herein.

As used herein and in the appended claims, the singular form "a," "an," and "the" include plural references unless the context clearly dictates otherwise. For example, a reference to "an anti-CTGF agent" includes a plurality of such agents; a reference to an "an anti-CTGF antibody" is a reference to one or more antibodies and to equivalents thereof known to those skilled in the art; and so forth.

The use of "including," "comprising," "having," "containing," or "involving" and variations thereof herein, is meant to encompass the items listed thereafter and equivalents thereof as well as additional items.

As used herein, the term "about" refers to ±10% of the numerical value of the number with which it is being used. Therefore, a dose of gemcitabine of about 1,000 mg/m$^2$ means a dose in the range of 900-1,100 mg/m$^2$.

When trade names are used herein, it is intended that the trade names independently encompass the trade name product and the active pharmaceutical ingredient(s) of the trade name product.

As used herein, the terms "subject," "individual," and "patient" are used interchangeably to refer to a mammal. In a preferred embodiment, the mammal is a primate, and more preferably a human being.

As used herein, the term "blood" encompasses whole blood, serum or plasma. When a specific antibody concentration in the blood is discussed, it is to be understood to include the antibody concentration in whole blood, serum or plasma.

As used herein, the terms "tumor" and "tumor mass" are synonymous and refer to a malignant growth having the properties of anaplasia and invasiveness with the propensity to metastasize.

As used herein, the terms "locally advanced pancreatic cancer" and "LAPC" describes a tumor that originates in the pancreas, but has grown beyond the confines of the pancreas, however, distant metastases are absent. LAPC includes tumors that arise in pancreatic exocrine or neuroendocrine tissue. LAPCs that originate from exocrine tissue comprise acinar cell carcinomas, adenocarcinomas, adenosquamous carcinomas, ampullary cancers, colloid carcinomas, giant cell tumors, hepatoid carcinomas, intraductal papillary-mucinous neoplasms, mucinous cystadenocarcinomas, pancreatoblastomas, serous cystadenocarcinomas, signet ring cell carcinomas, solid and pseudopapillary tumors, and undifferentiated carcinomas. LAPCs that originate from neuroendocrine tissue comprise gastrinomas, glucagonomas, insulinomas, nonfunctional islet cell tumors, somatostatinomas and vasoactive intestinal peptide-releasing tumors. In some embodiments, the LAPC is an adenocarcinoma. In further embodiments, the adenocarcinoma is ductal adenocarcinoma, also known as pancreatic ductal adenocarcinoma (PDAC).

A diagnosis of LAPC can be made based on the results obtained radiographically, e.g., contrast-enhanced thin-slice abdominal CT, endoscopic ultrasound, laparoscopic examination, histology, combinations thereof, or by other acceptable means.

A "resectable" LAPC is defined as a tumor that has no evidence of superior mesenteric vein (SMV) or portal vein (PV) abutment. Further there is no evidence of tumor thrombus or venous encasement. Additionally, clear fat planes are apparent around the celiac axis, hepatic artery and superior mesenteric artery (SMA). Resectable tumors are good candidates for resection.

A "borderline resectable" LAPC is defined as a tumor with venous involvement of the SMV or PV demonstrating tumor abutment with or without impingement and narrowing of the lumen. Additionally, the SMV or PV can be encased but there is no encasement of the nearby arteries, or short segments of venous occlusion resulting from either tumor thrombus or encasement. Further there is suitable vessel proximal and distal to the area of vessel involvement, allowing for safe resection and reconstruction. In addition, if tumor abutments the SMA, it does not to exceed 180 degrees of the circumference of the vessel wall. Gastroduodenal artery encasement may also be apparent with encasement up to the hepatic artery with either short segment encasement or direct abutment of the hepatic artery, without extension to the celiac axis. Borderline resectable tumors may be candidates for resection.

An "unresectable" LAPC is defined as a tumor having major venous thrombosis of the PV or SMV extending for several centimeters. Additionally, unresectable tumor further includes those that circumferential encase the SMA, celiac axis, proximal hepatic artery or the confluence of the PV, splenic vein (SV) and SMV. Unresectable tumors are not candidates for resection.

As used herein, the term "induction therapy" describes a therapy used to "downstage" a tumor i.e., reduce the size and/or stage of a tumor. In the context of LAPC, induction therapy is usually used to convert an unresectable tumor into at a borderline resectable tumor or a resectable tumor. Induction therapy can also be used to convert a borderline resectable tumor into a resectable tumor. In some embodiments, induction therapy is used to change a physiologic characteristic of a tumor, e.g., reduce desmoplasia to facilitate surgery. Typically, induction therapy is administered as a neoadjuvant therapy, i.e., prior, to a main therapy, for example chemotherapy, radiotherapy, chemoradiotherapy, surgery or hormone therapy. In other embodiments, induction therapy may be administered to reduce tumor cell number and/or viability including microscopic disease found at and beyond the tumor margin. In further embodiments, induction therapy may be administered to improve surgical margins. In additionally embodiments, induction therapy may be used as a first-line therapy, second-line therapy or salvage therapy. In other embodiments, induction therapy may be used to treat metastatic disease or to relieve one or more symptoms associated with pancreatic cancer, for example, reduce pain or gastric outlet obstruction associated with pancreatic cancer.

As used herein, the terms "convert" and "converting" as they apply to a tumor or LAPC mean to change, transform or otherwise modify the tumor or LAPC. For example, converting (downstaging) an unresectable LAPC to a resectable LAPC means changing or transforming the LAPC to a sufficient degree so that the LAPC is now resectable. Typically, conversion is achieved by a reduction in tumor size, reduction in the degree of normal tissue or normal vasculature that is abutted, encased or encompassed by tumor tissue, and/or a reduction in tumor desmoplasia.

In the context of treating LAPC that at initial diagnosis is classified as resectable, induction therapy comprising an anti-CTGF agent may facility resection of the tumor mass by shrinking the size of the tumor or reducing the degree of tumor desmoplasia. Induction therapy comprising an anti-CTGF agent may also increase the likelihood that R0 margins are achieved by substantially reducing or eliminating microscopic tumor cell deposits that may exist in normal tissue that is adjacent to the tumor. Further, induction therapy comprising an anti-CTGF agent may treat occult disease, including micrometastatic disease residing in locoregional lymph nodes.

In the context of treating a LAPC that at initial diagnosis is classified as borderline resectable, induction therapy comprising an anti-CTGF agent may eliminate or substantially reduce SMV or portal vein encasement or abutment. Additionally, induction therapy comprising an anti-CTGF agent may substantially reverse tumor thrombus. Further, clear fat planes may reappear around the celiac axis, hepatic artery and SMA. The elimination of at least venous encasement or abutment is sufficient to convert the status of a borderline resectable LAPC to resectable LAPC status. Patients that present with borderline resectable LAPC may further benefit from induction therapy comprising an anti-CTGF agent through the reduction or eradication of occult disease, including micrometastatic disease residing in the locoregional lymph nodes. Induction therapy comprising an anti-CTGF agent may also increase the likelihood that R0 margins are achieved with surgery.

In the context of treating a LAPC that at initial diagnosis is classified as unresectable, induction therapy comprising an anti-CTGF agent may substantially reduce or reverse major venous thrombosis of the PV or SMV. Further, induction therapy comprising an anti-CTGF agent may substantially reduce encasement of the SMA, celiac axis, proximal hepatic artery or the confluence of the PV, splenic vein (SV) and SMV to less than 180 degrees. If these conditions are achieved and there exists suitable vessel proximal and distal to the area of vessel involvement to allow for safe resection and reconstruction, then the changes achieved with induction therapy comprising an anti-CTGF agent are sufficient to convert an unresectable LAPC into borderline resectable LAPC status.

If induction therapy comprising an anti-CTGF agent substantially reduces or eliminates SMV or PV encasement or abutment, and optionally, reverses tumor thrombus or allows the development of clear fat planes around the celiac axis, hepatic artery and SMA, then the change is sufficient to convert an unresectable LAPC to resectable LAPC status. Further, induction therapy comprising an anti-CTGF agent may treat occult disease, including micrometastatic disease residing in locoregional lymph nodes. Induction therapy comprising an anti-CTGF agent may also increase the likelihood that R0 margins are achieved with surgery.

As used herein, "survival" refers to the patient remaining alive, and includes disease-free survival (DFS), progression free survival (PFS) and overall survival (OS). Survival can be estimated by the Kaplan-Meier method with differences in survival computed using the stratified log-rank test or other suitable means.

"Disease-free survival" and "DFS" refer to the patient remaining alive, without return of the cancer, for a defined period of time from initiation of treatment or from initial diagnosis until recurrence of the disease or death from any cause. In some embodiments, DFS is analyzed according to the intent-to-treat principle.

"Progression free survival" and "PFS" refer to the length of time from the start of treatment that a patient lives with the disease but it does not get worse, i.e., disease progression, or death from any cause.

"Overall survival" and "OS" refer to the patient remaining alive for a defined period of time from initiation of treatment or from initial diagnosis until death from any cause. In some embodiments, OS is analyzed according to the intent-to-treat principle.

"Time to tumor progression" and "TTP" are defined as the time from start of therapy until clinical and/or radiological progression of the disease. In some embodiments, TTP is measured from the time of tumor resection.

The methods of the invention are accomplished by administering to a subject in need thereof an effective amount of an induction therapy comprising an anti-CTGF agent. As used herein, the terms "anti-connective tissue growth factor agent" or "anti-CTGF agent" refer to any agent, molecule, macromolecule, compound, or composition that directly inhibits or decreases the expression of the CTGF gene or CTGF mRNA, or directly inhibits or decreases the activity or function of the CTGF protein. Anti-CTGF agents that are capable of directly inhibiting or reducing the expression of the CTGF gene include anti-CTGF oligonucleotides comprising antisense oligonucleotides, siRNA, shRNA and miRNA. In some embodiments, the anti-CTGF agents bind to CTGF and neutralize, block, inhibit, abrogate, reduce, antagonize or interfer with CTGF activity or function. Anti-CTGF agents capable of binding to CTGF include, without limitation, anti-CTGF antibodies, anti-CTGF antigen-binding fragments derived from antibodies, anti-CTGF antibody mimetics, and other CTGF binding polypeptides, peptides, oligonucleotides and non-peptide small molecules, for example aptamers. Anti-CTGF agents that bind to CTGF can block its interaction with cofactors including TGF-β or bone morphogenic protein 4 (BMP-4); membrane-associated proteins such as integrins, tyrosine kinase receptor type A (TrkA) or low density lipoprotein receptor-related protein 1 (LRP1). Additionally, anti-CTGF agents that bind to CTGF can block its interaction with membrane-associated protein or extracellular matrix components including heparin sulfate proteoglycans or fibronectin.

The anti-CTGF agents relied upon in the invention exert their effects directly and specifically on the CTGF gene, CTGF mRNA or CTGF protein, rather than through a non-specific inhibitory mechanism such as non-specific inhibition of transcription. Anti-CTGF agents further exclude agents that are inhibitors of a component of an upstream or downstream signaling pathway for CTGF, for example losartan, an angiotensin II receptor antagonist.

Antibodies

The term "antibody" is used in the broadest sense and specifically covers monoclonal antibodies (including full length monoclonal antibodies), polyclonal antibodies, multispecific antibodies (e.g., bispecific antibodies), and antibody fragments, so long as they exhibit the desired biological activity, and antibody mimetics.

The term "monoclonal antibody" as used herein refers to an antibody obtained from a population of substantially homogeneous antibodies, i.e., the individual antibodies comprising the population are identical except for possible mutations, e.g., naturally occurring mutations, that may be present in minor amounts. Thus, the modifier "monoclonal" indicates the character of the antibody as not being a mixture of discrete antibodies. In certain embodiments, a monoclonal antibody typically includes an antibody comprising a polypeptide sequence that binds a target, wherein the target-binding polypeptide sequence was obtained by a process that includes the selection of a single target binding polypeptide sequence from a plurality of polypeptide sequences. For example, the selection process can be the selection of a unique clone from a plurality of clones, such as a pool of hybridoma clones, phage clones, or recombinant DNA clones. It should be understood that a selected target binding sequence can be further altered, for example, to improve affinity for the target, to humanize the target binding sequence, to improve its production in cell culture, to reduce its immunogenicity in vivo, to create a multispecific antibody, etc., and that an antibody comprising the altered target binding sequence is also a monoclonal antibody of this invention. In contrast to polyclonal antibody preparations, which typically include different antibodies directed against different determinants (epitopes), each monoclonal antibody of a monoclonal antibody preparation is directed against a single determinant on an antigen.

The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including, for example, the hybridoma method (e.g., Kohler and Milstein, Nature, 256:495-97 (1975); Harlow et al., Antibodies: A Laboratory Manual (Cold Spring Harbor Laboratory Press, 2nd ed. 1988); recombinant DNA methods (see, e.g., U.S. Pat. No. 4,816, 567); phage-display technologies (see, e.g., Clackson et al., Nature, 352: 624-628 (1991); Marks et al., J Mol Biol 222:581-597 (1992); and Lee et al., J Immunol Methods 284(1-2): 119-132(2004), and technologies for producing human or human-like antibodies in animals that have parts or all of the human immunoglobulin loci or genes encoding human immunoglobulin sequences (see, e.g., WO 1998/24893; WO 1996/34096; WO 1996/33735; WO 1991/10741; Jakobovits et al., Proc Natl Acad Sci USA 90: 2551 (1993); U.S. Pat. Nos. 5,545,807; 5,545,806; 5,569,825; 5,625,126; 5,633,425; and 5,661,016).

Monoclonal antibodies specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass (see, e.g., U.S. Pat. No. 4,816,567; and Morrison et al., Proc Acad Sci USA 81:6851-6855 (1984).

"Humanized" forms of non-human (e.g., murine) antibodies are chimeric antibodies that contain minimal sequence derived from non-human immunoglobulin. In some embodiments, a humanized antibody is a human immunoglobulin (recipient antibody) in which residues from a one or more hypervariable regions (HVRs) of the recipient are replaced by residues from one or more HVRs of a non-human species (donor antibody) such as mouse, rat, rabbit, or nonhuman primate having the desired specificity, affinity, and/or capacity. For further details, see, e.g., Jones et al., Nature 321:522-525 (1986); Riechmann et al., Nature 332:323-329 (1988); and U.S. Pat. Nos. 6,982,321 and 7,087,409.

A "human antibody" is one which possesses an amino acid sequence which corresponds to that of an antibody produced by a human and/or has been made using any of the techniques for making human antibodies (see e.g., Hoogenboom and Winter, J. Mol Biol., 227:381 (1991); Marks et al., J. Mol Biol., 222:581 (1991); Boerner et al., J. Immunol., 147(1):86-95 (1991); Li et al., *Proc. Natl Acad. Sci. USA*, 103:3557-3562 (2006) and U.S. Pat. Nos. 6,075,181 and 6,150,584).

The term "isolated," as used herein, describes an antibody, antibody fragment, or antibody mimetic that is not in its natural milieu. No particular level of purification is required. Recombinantly produced molecules are considered isolated for purposes of the invention, as are native molecules, e.g., polyclonal antibodies, that have been separated, fractionated, or partially or substantially purified by any suitable technique.

A "naked antibody" for the purposes herein is an antibody that is not conjugated to a cytotoxic moiety or radiolabel. In some embodiments, the anti-CTGF antibody is a naked antibody.

The anti-CTGF antibodies of the invention may be specific for CTGF endogenous to the species of the subject to be treated or may be cross-reactive with CTGF from one or more other species. In some embodiments, the antibody for use in the present methods is obtained from the same species as the subject in need. In other embodiments, the antibody is a chimeric antibody wherein the constant domains are obtained from the same species as the subject in need and the variable domains are obtained from another species. For example, in treating a human subject, the antibody for use in the present methods may be a chimeric antibody having constant domains that are human in origin and variable domains that are mouse in origin. In preferred embodiments, the antibody for use in the present methods binds specifically to the CTGF endogenous to the species of the subject in need. Thus, in certain embodiments, the antibody is a human or humanized antibody, particularly a monoclonal antibody, that specifically binds human CTGF (GenBank Accession No. NP_001892).

Exemplary anti-CTGF antibodies for use in the induction therapies of the present invention are described. e.g., in U.S. Pat. No. 5,408,040; U.S. Patent Appl. No. 2014/0343258; PCT/US1998/016423; PCT/US1999/029652; International Publication Nos. WO 99/33878 and WO 2013/108869. Preferably, the anti-CTGF antibody, for use in the induction therapies of the invention, is a monoclonal antibody. Preferably the antibody is a neutralizing antibody. In particular embodiments, the antibody is identical to the antibody described and claimed in U.S. Pat. Nos. 7,405,274 and 7,871,617. In some embodiments, the anti-CTGF antibody for use the induction therapies of the invention has the identical amino acid sequence as the antibody produced by the cell line identified by ATCC Accession No. PTA-6006. In other embodiments, the antibody binds to CTGF competitively with an antibody produced by ATCC Accession No. PTA-6006. In further embodiments, the antibody binds to the same epitope as the antibody produced by ATCC Accession No. PTA-6006. A particular antibody for use in the methods of the invention is CLN-1 or mAb1 as described in U.S. Pat. No. 7,405,274 or an antibody substantially equivalent thereto or derived therefrom. Variants of CLN-1 that retain the binding and neutralization functions characteristic of CLN-1 are also useful in the present invention. Such variants typically retain the variable regions of the heavy and/or light chain of the original neutralizing antibody, or minimally the complementarily determining regions (CDR) of heavy and light chains, and may contain substitutions and/or deletions in the amino acid sequences outside of those variable regions.

Antibody CLN1 is produced by the cell line defined by ATCC Accession No. PTA-6006, deposited with the American Type Culture Collection (ATCC, 10801 University Boulevard, Manassas, Va. 20110-2209) on 20 May 2004.

As referred to herein, the phrase "an antibody that specifically binds to CTGF" includes any antibody that binds to CTGF with high affinity. Affinity can be calculated from the following equation:

$$\text{Affinity} = K_a = \frac{[Ab \cdot Ag]}{[Ab][Ag]} = \frac{1}{K_d}$$

where [Ab] is the concentration of the free antigen binding site on the antibody, [Ag] is the concentration of the free antigen, [Ab·Ag] is the concentration of occupied antigen binding sites, $K_a$ is the association constant of the complex of antigen with antigen binding site, and $K_d$ is the dissociation constant of the complex. A high-affinity antibody typically has an affinity at least on the order of $10^8$ M$^{-1}$, $10^9$ M$^{-1}$ or $10^{10}$ M$^{-1}$. In particular embodiments, an antibody for use in the present methods will have a binding affinity for CTGF between of $10^8$M$^{-1}$ and $10^{10}$ M$^{-1}$, between $10^8$ M$^{-1}$ and $10^9$M$^{-1}$ or between $10^9$ M$^{-1}$ and $10^{10}$ M$^{-1}$. In some embodiments the high-affinity antibody has an affinity of about $10^8$ M$^{-1}$, $10^9$ M$^{-1}$ or $10^{10}$ M$^{-1}$.

"Antibody fragments" comprise a functional fragment or portion of an intact antibody, preferably comprising an antigen binding region thereof. A functional fragment of an antibody will be a fragment with similar (not necessarily identical) specificity and affinity to the antibody which it is derived. Non-limiting examples of antibody fragments include Fab, F(ab')$_2$, and Fv fragments that can be produced through enzymatic digestion of whole antibodies, e.g., digestion with papain, to produce Fab fragments. Other non-limiting examples include engineered antibody fragments such as diabodies (Holliger P et al. *Proc Natl Acad Sci USA*. 1993, 90; 6444-6448); linear antibodies (Zapata et al. 1995 *Protein Eng*, 8(10):1057-1062); single-chain antibody molecules (Bird K D et al. *Science*, 1988, 242: 423-426); single domain antibodies, also known as nanobodies (Ghahoudi M A et al. *FEBS Lett.* 1997, 414: 521-526); domain antibodies (Ward E S et al. *Nature*. 1989, 341: 544-546); and multispecific antibodies formed from antibody fragments. Fragments and engineered versions of a neutralizing antibody, e.g., Fab, F(ab)2, Fv, scFV, diabodies, triabodies, minibodies, nanobodies, chimeric antibodies, humanized antibodies, etc. are as useful in the method of the present invention as the parent antibody from which the fragments and engineered antibodies were derived.

Antibody Mimetics

Antibody mimetics are proteins, typically in the range of 3-25 kD, that are designed to bind an antigen with high specificity and affinity like an antibody, but are structurally unrelated to antibodies. Frequently, antibody mimetics are based on a structural motif or scaffold that can be found as a single or repeated domain from a larger biomolecule. Examples of domain-derived antibody mimetics include AdNectins that utilize the 10th fibronectin III domain (Lipovšek D. *Protein Eng Des Sel*, 2010, 24:3-9); Affibodies that utilize the Z domain of *staphylococcal* protein A (Nord K et al. *Nat Biotechnol*. 1997, 15: 772-777), and DARPins that utilize the consensus ankyrin repeat domain (Amstutz P. *Protein Eng Des Sel.* 2006, 19:219-229). Alternatively, antibody mimetics can also be based on the entire structure of a smaller biomolecule, such as Anticalins that utilize the lipocalin structure (Beste G et al. *Proc Natl Acad Sci USA*.

1999, 5:1898-1903). In some embodiments, the anti-CTGF antibody is an antibody mimetic.

Oligonucleotides

The term "oligonucleotide" refers to oligomers or polymers of ribonucleic acid (RNA), deoxyribonucleic acid (DNA), mimetics or analogs of RNA or DNA, or combinations thereof. Oligonucleotides are molecules formed by the covalent linkage of two or more nucleotides or their analogs. Unless otherwise indicated, a particular nucleic acid sequence in addition to explicitly indicating the disclosed sequence also implicitly encompasses conservatively modified variants thereof (e.g., degenerate codon substitutions), alleles, and complementary sequences.

Anti-CTGF oligonucleotides useful for practicing the methods of the invention comprise antisense oligonucleotides, ribozymes, external guide sequence (EGS) oligonucleotides (oligozymes) and inhibitory RNA (RNAi) including siRNA, miRNA (microRNA), and short hairpin RNA (shRNA).

In some embodiments, the administration of an anti-CTGF oligonucleotide decreases the expression of CTGF mRNA. In particular embodiments, the decrease in the expression of CTGF mRNA comprises the interference in the function of the CTGF DNA sequence (CTGF gene), typically resulting in decreased replication and/or transcription of the CTGF DNA. In other embodiments, the decrease in expression of CTGF mRNA by an anti-CTGF oligonucleotide comprises the interference in function of CTGF RNA, typically resulting in impaired splicing of transcribed CTGF RNA (pre-mRNA) to yield mature mRNA species, decreased CTGF RNA stability, decreased translocation of the CTGF mRNA to the site of protein translation and impaired translation of protein from mature mRNA. In other embodiments, the decrease in expression of CTGF mRNA by an anti-CTGF oligonucleotide comprises the decrease in cellular CTGF mRNA number or cellular content of CTGF mRNA. In some embodiments, the decrease in expression of CTGF mRNA by an anti-CTGF oligonucleotide comprises the down-regulation or knockdown of CTGF gene expression. In other embodiments, the decrease in expression of CTGF mRNA by an anti-CTGF oligonucleotide comprises the decrease in CTGF protein expression or cellular CTGF protein content. In some embodiments, the methods of the invention comprise the administration of synthetic oligonucleotides that decrease the expression of human CTGF mRNA or human CTGF protein.

In some embodiments, the administration of an effective amount of an induction therapy comprising an anti-CTGF oligonucleotide decreases CTGF mRNA transcription rate, cellular CTGF mRNA level, CTGF expression rate or cellular CTGF protein level of PC cells or tumor-associated pancreatic stellate cells by at least 5%, at least 10%, at least 15%, at least 20%, at least 25%, at least 30%, at least 35%, at least 40%, at least 45%, at least 50%, at least 60%, at least 70%, at least 80% or at least 90% compared to controls. In additional embodiments, the administration of an effective amount of an induction therapy comprising an anti-CTGF oligonucleotide decreases tumor interstitial CTGF protein by at least 5%, at least 10%, at least 15%, at least 20%, at least 25%, at least 30%, at least 35%, at least 40%, at least 45%, at least 50%, at least 60%, at least 70%, at least 80% or at least 90% compared to controls. In further embodiments, the administration of an effective amount of an induction therapy comprising an anti-CTGF oligonucleotide decreases or reverses PC fibrosis or desmoplasia. In other embodiments, the administration of an effective amount of an induction therapy comprising an anti-CTGF oligonucleotide increases. PC responsiveness to chemotherapy, chemoradiotherapy and/or radiotherapy.

In some embodiments, the anti-CTGF oligonucleotide is an antisense oligonucleotide. As used herein, the terms "antisense oligonucleotide" and "ASO" refer to an oligomeric nucleic acid that is capable of hybridizing with its complementary target nucleic acid sequence resulting in the modulation of the normal function of the target nucleic acid sequence.

Anti-CTGF antisense oligonucleotides useful in practicing the methods of the invention comprise contiguous nucleotide sequences between 8 to 50 nucleotides in length, more preferably, between 10 and 30, between 12 and 25, between 12 to 20, between 13 and 24 or between 16 and 21 nucleotides in length. Preferred antisense oligonucleotides to CTGF for use in the methods of the invention include those disclosed in PCT/US2002/038618, PCT/US2009/054973 and PCT/US2009/054974; U.S. Pat. Nos. 6,358,741 6,965,025; and 8,802,839.

In some embodiments, the anti-CTGF oligonucleotide is a small interfering RNA (siRNA). The terms "small interfering RNA" or "siRNA" refer to single- or double-stranded RNA molecules that induce the RNA interference pathway and act in concert with host proteins, e.g., RNA induced silencing complex (RISC) to degrade mRNA in a sequence-dependent fashion. Preferred siRNA oligonucleotides to CTGF useful in the methods of the invention include U.S. Pat. Nos. 8,138,329, 7,622,454 and 7,666,853; and PCT/US2011/029849 and PCT/US2011/029867.

In some embodiments, the anti-CTGF oligonucleotide is a microRNA (miRNA). The terms "microRNA" or "miRNA" refer to oligonucleotides that are post-transcriptional regulators that bind to complementary sequences on target messenger RNA transcripts (mRNAs), usually resulting in translational repression or target degradation and gene silencing. Typically, miRNAs are about 21-23 nucleotides in length and bind to the 3'-untranslated regions (3'-UTRs) of target mRNAs.

In some embodiments, the anti-CTGF oligonucleotide is a ribozyme (Ryu and Lee S-W. *J Biochem Mol Bio.* 2003; 36:538-544.) In other embodiments, the oligonucleotide is an external guide sequence (EGS) oligonucleotide that upon hybridization with its complimentary mRNA sequence, the complex is targeted for cleavage by RNase P. (Yuan Y and Altman S. *Science* 1994, 263:1269-1273; Nadal A et al. *J Biol Chem.* 2002; 277:30606-30613.)

Typically, anti-CTGF oligonucleotides are synthesized using one or more modified nucleotides. As used herein, the terms "modified" and "modification" when used in the context of the constituents of a nucleotide monomer, i.e., sugar, nucleobase and internucleoside linkage (backbone), refer to non-natural changes to the chemical structure of these naturally occurring constituents or the substitutions of these constituents with non-naturally occurring ones, i.e., mimetics. For example, the "unmodified" or "naturally occurring" sugar ribose (RNA) can be modified by replacing the hydrogen at the 2'-position of ribose with a methyl group. See Monia, B. P. et al. *J Biol. Chem.*, 268: 14514-14522, 1993. Similarly, the naturally occurring internucleoside linkage is a 3' to 5' phosphodiester linkage that can be modified by replacing one of the non-bridging phosphate oxygen atoms with a sulfur atom to create a phosphorothioate linkage. See Geiser T. *Ann NY Acad Sci.* 616: 173-183, 1990. Modified oligonucleotides are structurally distinguishable, but functionally interchangeable with naturally occurring or synthetic unmodified oligonucleotides and usually have enhanced properties such as increased resistance to degradation by exonucleases and endonucleases, or increased binding affinity.

Non-naturally occurring internucleoside linkages "oligonucleotide backbones" include those that retain a phosphorus atom and also those that do not have a phosphorus atom. Numerous phosphorous containing modified oligonucleotide backbones are known in the art and include, for example, phosphoramidites, phosphorodiamidate morpholinos, phosphorothioates, phosphorodithioates, phosphotriesters, aminoalkylphosphotri-esters, methyl and other alkyl phosphonates including 3'-alkylene phosphonates, 5'-alkylene phosphonates and chiral phosphonates, and phosphinates. In some embodiments, the modified oligonucleotide backbones are without phosphorus atoms and comprise short chain alkyl or cycloalkyl internueleoside linkages, mixed heteroatom and alkyl or cycloalkyl internucleoside linkages, or one or more short chain heteroatomic or heterocyclic internucleoside linkages. See Swayze E. and Bhat B. in *Antisense Drug Technology Principles, Strategies, and Applications.* 2nd Ed. CRC Press, Boca Rotan Fla. 2008 p. 144-182.

In further embodiments, the non-naturally occurring internucleoside linkages are uncharged and in others, the linkages are achiral. In some embodiments, the non-naturally occurring internucleoside linkages are uncharged and achiral, e.g., peptide nucleic acids (PNAs).

In some embodiments, the modified sugar moiety is a sugar other than ribose or deoxyribose. In particular embodiments, the sugar is arabinose, xylulose or hexose. In further embodiments, the sugar is substituted with one of the following at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted C1 to C10 alkyl or C2 to C10 alkenyl and alkynyl. In some embodiments, the modifications include 2'-methoxy (2'-O—CH3), 2'-aminopropoxy (2'-OCH2CH2CH2NH2), 2'-allyl (2'-CH2-CH=CH2), 2'-O-allyl (2'-O—CH2-CH=CH2) and 2'-fluoro (2'-F). The 2'-modification may be in the arabino (up) position or ribo (down) position. Similar modifications may also be made at other positions on an oligonucleotide, particularly the 3' position of the sugar on the 3' terminal nucleotide or in 2'-5' linked oligonucleotides and the 5' position of 5' terminal nucleotide.

In some embodiments, the modified sugar is conformationally restricted. In further embodiments, the conformational restriction is the result of the sugar possessing a bicyclic moiety. In still further embodiments, the bicyclic moiety links the 2'-oxygen and the 3' or 4'-carbon atoms. In some embodiments the linkage is a methylene (—CH2-)n group bridging the 2' oxygen atom and the 4' carbon atom, wherein n is 1 or 2. This type of structural arrangement produces what are known as "locked nucleic acids" (LNAs). See Koshkin et al. *Tetrahedron,* 54, 3607-3630, 1998; and Singh et al., *Chem Commun,* 455-456, 1998.

In some embodiments, the modified sugar moiety is a sugar mimetic that comprises a morpholino ring. In further embodiments, the phosphodiester internucleoside linkage is replaced with an uncharged phosphorodiamidate linkage. See Summerton, *Antisense Nucleic Acid Drug Dev.,* 7: 187-195,1997.

In some embodiments, both the phosphate groups and the sugar moieties are replaced with a polyamide backbone comprising repeating N-(2-aminoethyl)-glycine units to which the nucleobases are attached via methylene carbonyl linkers. These constructs are called peptide nucleic acids (PNAs). PNAs are achiral, uncharged and because of the peptide bonds, are resistant to endo- and exonucleases. See Nielsen et al., *Science,* 1991, 254, 1497-1500 and U.S. Pat. No. 5,539,082.

Oligonucleotides useful in the methods of the invention include those comprising entirely or partially of naturally occurring nucleobases. Naturally occurring nucleobases include adenine, guanine, thymine, cytosine, uracil, 5-methylcytidine, pseudouridine, dihydrouridine, inosine, ribothymidine, 7-methylguanosine, hypoxanthine and xanthine.

Oligonucleotides further include those comprising entirely or partially of modified nucleobases (semi-synthetically or synthetically derived). Modified nucleobases include 5-methylcytosine (5-me-C), 5-hydroxymethyl cytosine, hypoxanthine, 2-aminoadenine, 2-methyladenine, 6-methyladenine, 2-propyladenine, N6-adenine, N6-isopentenyladenine, 2-methylthio-N6-isopentenyladenine, 2-methylguanine, 6-methylguanine, 2-propylguanine, 1-methylguanine, 7-methylguanine, 2,2-dimethylguanine, 2-thiouracil, 2-thiothymine and 2-thiocytosine, 5-fluorouracil, 5-bromouracil, 5-chlorouracil, 5-iodouracil, dihydrouracil, 5-methyl-2-thiouracil, 2-thiouracil, 4-thiouracil, 5-methyluracil, uracil-5-oxyacetic acid methylester, uracil-5-oxyacetic acid, 5-carboxymethylaminomethyl-2-thiouridine, hypoxanthine, xantine, 4-acetylcytosine, 5-(carboxyhydroxylmethyl) uracil, 5-methoxycarboxymethyluracil, 5-methoxyuracil, 5-methyl-2-thiouracil, 3-(3-amino-3-N-2-carboxypropyl) uracil, 5-carboxymethylaminomethyluracil, 5-methylaminomethyluracil, 5-methoxyaminomethyl-2-thiouracil, 5-propynyl uracil and cytosine and other alkynyl derivatives of pyrimidine bases, 6-azo uracil, cytosine and thymine, 5-uracil (pseudouracil), 4-thiouracil, 8-halo-adenine, 8-amino adenine, 8-thiol adenine, 8-thioalkyl adenine, 8-hydroxyl adenine, 5-halo particularly 5-bromo, 5-trifluoromethyl uracil, 3-methylcytosine, 5-methylcytosine, 5-trifluoromethyl cytosine, 7-methylguanine and 7-methyladenine, 2-F-adenine, 2-amino-adenine, 8-azaguanine and 8-azaadenine, 7-deazaguanine, 8-halo-guanine, 8-amino guanine, 8-thiol guanine, 8-thioalkyl guanine, 8-hydroxyl guanine, 7-deazaadenine, 3-deazaguanine, 3-deazaadenine, beta-D-galactosylqueosine, beta-D-mannosylqueosine, inosine, 1-methylinosine, 2,6-diaminopurine and queosine. Further modified nucleobases include tricyclic pyrimidines such as phenoxazine cytidine(1H-pyrimido[5,4-b][1,4]benzoxazin-2(3H)-one), and phenothiazine cytidine (1H-pyrimido[5,4-b][1,4]benzothiazin-2(3H)-one. See Herdewijn P, *Antisense Nucleic Acid Drug Dev* 10: 297-310, 2000; and Sanghvi Y S, et al. *Nucleic Acids Res,* 21: 3197-3203, 1993.

The aforementioned modifications may be incorporated uniformly across an entire oligonucleotide, at specific regions or discrete locations within the oligonucleotide including at a single nucleotide. Incorporating these modifications can create chimeric or hybrid oligonucleotides wherein two or more chemically distinct areas exist, each made up of one or more nucleotides.

In some embodiments, the oligonucleotides further comprise a heterogeneous molecule covalently attached to the oligomer, with or without the use of a linker, also known as a crosslinker. In some embodiments, the heterogeneous molecule is a delivery or internalization moiety that enhances or assists the absorption, distribution and/or cellular uptake of the oligonucleotides. These moieties include polyethylene glycols, cholesterols, phospholipids, cell-penetrating peptides (CPPs) ligands to cell membrane receptors and antibodies. See Manoharan M. in *Antisense Drug Tech-* nology: Principles, Strategies and Applications, Crooke S T, ed. Marcel Dekker, New York, N.Y., 2001, p. 391-470

Oligonucleotides useful in the methods of the invention may be conveniently and routinely made through the well-known technique of solid phase synthesis. Equipment for such synthesis is sold by several vendors including, for example, Life Technologies Corporation (Carlsbad, Calif.). Any other means for such synthesis known in the art may alternatively be employed.

In some embodiments, anti-CTGF oligonucleotides are delivered through the use of various recombinant vectors. In further embodiments, the recombinant expression vectors are DNA plasmids, while in other embodiments, the expression vectors are viral vectors or derived from viral vectors, including retrovirus and adeno-associated virus vectors. See, e.g., Gonzalez-Carmona M A et al. *J Hepatol.* 2011; 55(1): 19-28; Sakamoto N et al. *J Gastroenterol Hepatol.* 2008; 23(9):1437-1447. These genetic constructs can be formulated and administered according to established procedures within the art. In some embodiments, patients are administered recombinant expression vectors that encode a short hairpin anti-CTGF oligonucleotide. In other embodiments, the recombinant expression vectors encode anti-CTGF antisense oligonucleotides. In further embodiments, the expression vectors persist in target cells. In alternative embodiments, the vectors are repeatedly administered as necessary.

Chemotherapy Agents

In some embodiments, induction therapy comprising an anti-CTGF agent further comprises a chemotherapy agent. In still further embodiments, the chemotherapy agent is selected from the group consisting of antimetabolites, mitotic inhibitors, alkylating agents, including DNA cross-linking agents, topisomerase inhibitors, anti-tumor antibiotics, differentiating agents and hormones.

Antimetabolites

Antimetabolites are structural analogues of normal metabolites needed for metabolic activity, synthesis of nucleic acids, or DNA and RNA replication. Antimetabolites inhibit or prevent the function of normal metabolites and induce cell death during the S phase of cell growth when incorporated into RNA or DNA. Antimetabolites include analogues of folate, purine and pyrimidine.

In some embodiments of the present invention, the antimetabolite is a folate analogue (antifolate). In further embodiments, the folate analogue is selected from the group consisting of methotrexate, aminopterin, raltitrexed, trimethoprim, pyrimethamine and pemetrexed.

In some embodiments, the antimetabolite is a purine analogue (purine antagonist). In further embodiments, the purine analogue is selected from the group consisting of azathioprine, clofarabine, 6-mercaptopurine, 6-thioguanine, 2'-desoxycoformicine, fludarabinphosphate, pentostatin and 2-chlordeoxyadenosine.

In some embodiments, the antimetabolite is a pyrimidine analogue (pyrimidine antagonist). In further embodiments, the pyrimidine analogue is selected from the group consisting of 5-fluorouracil (5-FU), capecitabine, cytosine arabinoside, decitabine, difluorodesoxycytidine, floxuridine, gemcitabine and tegafur.

In other embodiments, induction therapy comprising an anti-CTGF agent further comprises the administration of gemcitabine at a dose of at least about 500 $mg/m^2$, 600 $mg/m^2$, 700 $mg/m^2$, 800 $mg/m^2$, 900 $mg/m^2$, 1,000 $mg/m^2$, 1,100 $mg/m^2$ or 1,200 $mg/m^2$. In further embodiments, gemcitabine is administered at a dose of no more than about 600 $mg/m^2$, 700 $mg/m^2$, 800 $mg/m^2$, 900 $mg/m^2$, 1,000 $mg/m^2$, 1,100 $mg/m^2$ or 1,200 $mg/m^2$. In additional embodiments, gemcitabine is administered at a dose of between 500 $mg/m^2$ to 1,200 $mg/m^2$, between 700 $mg/m^2$ to 1,100 $mg/m^2$, or 900 $mg/m^2$ to 1,100 $mg/m^2$. In particular embodiments, gemcitabine is administered at a dose of about 1,000 $mg/m^2$.

In some embodiments, the antimetabolite is a ribonucleotide reductase inhibitor (RNR inhibitor). In further embodiments, the RNR inhibitor is hydroxyurea.

Mitotic Inhibitors

Mitotic inhibitors, also known as antimitotics, are compounds that inhibit mitosis, for example, by inhibiting tubuline depolymerization. Many mitotic inhibitors, are well known in the art. In some embodiments, the mitotic inhibitor is selected from the group consisting of, taxenes, epothilones, nocodazole, colcemid, colchicine; and vinca alkaloids. Taxenes useful in the methods of the invention include docetaxel, larotaxel, ortataxel, tesetaxel, paclitaxel and nab-paclitaxel. In particular embodiments, the taxane is generically known as paclitaxel protein-bound particles for injectable suspension (albumin-bound) and marketed as ABRAXANE® (Celegene, Summit N.J.). Epothilones useful in the methods of the invention include ixabepilone (BMS-247550, aza-epothilone B, Ixempra), patupilone (EPO906, epothilone B), KOS-862 (desoxyepothilone B, epothilone D), BMS-310705, ZK-EPO (ZK-219477), and KOS-1584. Vinca alkaloids useful in the methods of the invention further include vinblastine, vinorelbine, vincristine, vindesine vinepidine, vinglycinate sulfate, vinleurosine sulfate, vinrosidine sulfate and vinzolidine sulfate.

In some embodiments of the present invention, the antimitotic is nanoparticle size. In further embodiments, the nanoparticle sized antimitotic is paclitaxel. In still further embodiments, the nanoparticle sized paclitaxel is bound to a carrier. In some embodiments, the carrier is a protein. In further embodiments, carrier protein is selected from the group consisting of insulin, hemoglobin, lysozyme, immunoglobulins, a-2-macroglobulin, fibronectin, vitronectin, fibrinogen, casein, albumin or combinations thereof. In particular embodiments, the carrier protein is albumin, preferably human albumin. In other embodiments, the carrier is a synthetic polymer. In further embodiments, the synthetic polymer is selected from the group consisting of polyalkylene glycols (e.g., linear or branched chain), polyvinyl alcohol, polyacrylates, polyhydroxyethyl methacrylate, polyacrylic acid, polyethyloxazoline, polyacrylamides, polyisopropyl acrylamides, polyvinyl pyrrolidinone, polylactide/glycolide and combinations thereof. In particular embodiments, the mitotic inhibitor is nab-paclitaxel (for example, ABRAXANE®, a suspension of nanoparticle sized paclitaxel that is bound to albumin and formulated for injection).

In some embodiments, induction therapy comprising an anti-CTGF agent further comprises the administration of a mitotic inhibitor at a dose of about 0.1 mg to about 10,000 mg, from about 1 mg to about 5,000 mg, from about 10 mg to about 2,500 mg, from about 50 mg to about 1,000 mg, from about 100 mg to about 500 mg, from about 100 mg to about 1,000 mg, from about 25 mg to about 2,000 mg or from about 500 mg to about 2,500 mg.

In additional embodiments, induction therapy comprising an anti-CTGF agent further comprises the administration of nab-paclitaxel at a dose of at least about 50 $mg/m^2$, 60 $mg/m^2$, 70 $mg/m^2$, 80 $mg/m^2$, 90 $mg/m^2$, 100 $mg/m^2$, 110 $mg/m^2$, 120 $mg/m^2$, 125 $mg/m^2$, 130 $mg/m^2$, 140 $mg/m^2$ or 150 $mg/m^2$. In other embodiments, the nab-paclitaxel is administered at a dose of not more than about 60 $mg/m^2$, 70 $mg/m^2$, 80 $mg/m^2$, 90 $mg/m^2$, 100 $mg/m^2$, 110 $mg/m^2$, 120 $mg/m^2$, 125 $mg/m^2$, 130 $mg/m^2$, 140 $mg/m^2$ or 150 $mg/m^2$.

In further embodiments, the nab-paclitaxel is administered at a dose of between 50 mg/m² to 150 mg/m², 70 mg/m² to 130 mg/m², 90 mg/m² to 125 mg/m², 100 mg/m² to 130 mg/m², 110 mg/m² to 130 mg/m² or 120 mg/m² to 130 mg/m². In particular embodiments, the nab-paclitaxel is administered at a dose of about 100 mg/m², 110 mg/m², 115 mg/m², 120 mg/m², 125 mg/m², 130 mg/m² or 135 mg/m².

Alkylating and DNA Crosslinking Agents

Alkylating and DNA crosslinking agents directly damage DNA and prevent cancer cells from reproducing. In some embodiments, alkylating agents for use in the methods of the invention include nitrogen mustards: such as bendamustine, estramustine, chlorambucil, cyclophosphamide, ifosfamide, mechlorethamine, melphalan, prednimustine trofosfamide, and uramustine. In other embodiments, the alkylating agents include nitrosoureas such as streptozocin, carmustine (BCNU), fotemustine, lomustine, nimustine, ranimustine, and semustine. In further embodiments, the alkylating agents include alkyl sulfonates such as busulfan, mannosulfan and treosulfan triazines including dacarbazine (DTIC) and temozolomide. In other embodiments, the alkylating agents are ethylenimines such as thiotepa and altretamine (hexamethylmelamine). Alkylating agents further include procarbazine, altretamine and mitobronitol.

In some embodiments, DNA crosslinking agents for use in the methods of the invention include the platinum drugs carboplatin, cisplatin, dexormaplatin, enloplatin, iproplatin, nedaplatin, ormaplatin oxaliplatin, picoplatin, satraplatin, spiroplatin, triplatin tetranitrate and zeniplatin.

Topisomerase Inhibitors

Topoisomerase inhibitors interfere with the enzymes topoisomerase I and/or II that catalyze the breaking and rejoining of the phosphodiester backbone of DNA strands. Inhibition of topoisomerase I and/or II block ligation of DNA strands leading to single and double stranded DNA breaks resulting in the induction of apoptosis. In some embodiments, topoisomerase I inhibitors for use in the methods of the invention include camptothecin derivatives, e.g., belotecan, rubitecan, topotecan and irinotecan (CPT-11). In some embodiments, topoisomerase inhibitors for use in the methods of the invention include etoposide (VP-16), teniposide and mitoxantrone.

Antitumor Antibiotics

Antitumor antibiotics are natural products typically produced by members of the genus *Streptamyres* that interfere with nucleic acid synthesis and/or function. Antitumor antibiotics include anthracyclines, anthracenediones and chromomycins. In some embodiments, anthracyclines for use in the methods of the invention include aclarubicin, amrubicin, daunorubicin, doxorubicin, epirubicin, idarubicin, pirarubicin, valrubicin and zorubicin. In other embodiments, anthracenediones for use in the methods of the invention include mitoxantrone, and pixantrone. Chromomycins include dactinomycin. Other useful antitumor antibiotics include actinomycin-D, ambomycin, anthramycin, azotomycin, bleomycin, cactinomycin, mitomycin-C and plicamycin.

Differentiating Agents

Differentiating agents force cancer cells to undergo differentiation into more mature phenotypes with resultant loss of proliferative capacity. In some embodiments, differentiating agents for use in the methods of the invention include retinoids (alitretinoin, tretinoin and bexarotene), sodium butyrate, phenylacetate and arsenic trioxide.

Hormones

Non-limiting, examples of hormonal agents that are useful in the methods of the present invention include aromatase inhibitors, selective estrogen receptor modulators (SERMs), and estrogen receptor antagonists. Aromatase inhibitors may be steroidal or nonsteroidal. Non-limiting examples of nonsteroidal aromates inhibitors include letrozole, anastrozole, aminoglutethimide, fadrozole, and vorozole. Non-limiting examples of steroidal aromatase inhibitors include aromasin (exemestane), formestane, and testolactone. Non-limiting examples of hormonal agents that are SERMs include tamoxifen, afimoxifene, arzoxifene, bazedoxifene, clomifene, femarelle, lasofoxifene, ormeloxifene, raloxifene, and toremifene. Non-limiting examples of hormonal agents that are estrogen receptor antagonists include fulvestrant. Other hormonal agents include but are not limited to abiraterone and lonaprisan.

Other Chemotherapeutic Agents

In some embodiments, an induction therapy comprising an anti-CTGF agent further comprises one or more chemotherapeutic agents selected from the group consisting of acivicin; aclarubicin; acodazole hydrochloride; acronine; adozelesin; aldesleukin; altretamine; ametantrone acetate; aminoglutethimide; amsacrine; anastrozole; asparaginase; asperlin; azacitidine; azetepa; batimastat; benzodepa; bicalutamide; bisantrene hydrochloride; bisnafide dimesylate; bizelesin; brequinar sodium; bropirimine; busulfan; calusterone; caracemide; carbetimer; carubicin hydrochloride; carzelesin; cedefingol; cirolemycin; cladribine; crisnatol mesylate; cytarabine; dacarbazine; dezaguanine; diaziquone; doxifluridine; droloxifene; dromostanolone propionate; duazomycin; edatrexate; eflornithine hydrochloride; elsamitrucin; enpromate; epipropidine; erbulozole; esorubicin hydrochloride; etanidazole; etoprine; fadrozole hydrochloride; fazarabine; fenretinide; fludarabine phosphate; flurocitabine; fosquidone; fostriecin sodium; ilmofosine; irinotecan hydrochloride; lanreotide acetate; leuprolide acetate; liarozole hydrochloride; lometrexol sodium; losoxantrone hydrochloride; masoprocol; maytansine; megestrol acetate; melengestrol acetate; menogaril; metoprine; meturedepa; mitindomide; mitocarcin; mitocromin; mitogillin; mitomalcin mitomycin; mitosper; mitotane; mitoxantrone hydrochloride; mycophenolic acid; nogalamycin; oxisuran; pegaspargase; peliomycin; pentamustine; peplomycin sulfate; perfosfamide; pipobroman; piposulfan; piroxantrone hydrochloride; plomestane; porfimer sodium; porfiromycin; puromycin; pyrazofurin; riboprine; rogletimide; safingol; simtrazene; sparfosate sodium; sparsomycin; spirogermanium hydrochloride; spiromustine; streptonigrin; sulofenur; talisomycin; tecogalan sodium; teloxantrone hydrochloride; temoporfin; teroxirone; thiamiprine; tiazofuirin; tioguanine; tirapazamine; trestolone acetate; triciribine phosphate; trimetrexate; trimetrexate glucuronate; triptorelin; tubulozole hydrochloride; uracil mustard; uredepa; vapreotide; verteporfin; vorozole; and zinostatin. Additional antineoplastic agents include those disclosed in Chapter 52, *Antineoplastic Agents* (Paul Calabresi and Bruce A. Chabner), and the introduction thereto, 1202-1263, of Goodman and Gilman's *The Pharmacological Basis of Therapeutics*, Eighth Edition, 1990, McGraw-Hill, Inc. (Health Professions Division).

In some embodiments, an induction therapy comprising an anti-CTGF agent comprises the administration of 5-fluorouracil, irinotecan and oxaliplatin (FOLFIRINOX); gemcitabine, docetaxel and capecitabine (GTX); gemcitabine and cisplatin; gemcitabine, 5-fluorouracil, leucovorin and cisplatin (G-FLIP) or 5-fluorouracil and mitomycin C.

Additional Therapeutic Agents

In some embodiments, an induction therapy comprising an anti-CTGF agent comprises an immunotherapy agent. Immunotherapy agent is defined broadly to include exogenously produced antibodies, such as anti-human extracellular matrix metalloproteinase inducer (EMMPRIN) antibody or bispecific T cell engaging antibody MT110; vaccines, including, peptide vaccines, whole tumor cell vaccines, antigen-pulsed dendritic cell-based vaccines and DNA vaccines; and adoptive cell transfer.

In other embodiments, an induction therapy comprising an anti-CTGF agent comprises an additional therapeutic agent selected from the group consisting of oncolytic viruses, such as HF10; ultrasound-guided high-intensity focused ultrasound therapeutic ablation; radiofrequency ablation (RFA), brachytherapy seeds; antisense oligonucleotides and siRNA to membrane-type 1 matrix metalloproteinase (MT1-MMP), TGF-β or Smad; COX-2 inhibitors such as celecoxib; statins, such as lovastatin; mTOR inhibitors such as sirolimus, temsirolimus, evorolimus, and deforolimus; farnesyltransferase inhibitors such as tipifarnib; pirfenidone; IGF-I antagonists such as an anti-IGF-1 antibody (e.g., AVE 1642 and IMC-A1 1); IGF-I kinase inhibitors; EGFR/HER-1 antagonists such as an anti-EGFR antibody (e.g., cetuximab, panitumamab); EGFR kinase inhibitors (e.g., erlotinib, gefitinib); Src/Abl antagonists such as bosutinib; proteasome inhibitors such as bortezomib; phosphodiesterase inhibitors such as anagrelide; inosine monophosphate dehydrogenase inhibitors such as tiazofurine; lipoxygenase inhibitors such as masoprocol; endothelin antagonists; interferons including interferon alfa-2a, interferon alfa-2b, interferon alfa-n1, interferon alfa-n3, interferon beta-I a and interferon gamma-I b; immune modulators such as lenalidomide, pomalidomide, or thalidomide; folinic acid or leucovorin calcium; integrin antagonists such as an integrin α5β1-antagonist (e.g., JSM6427); nuclear factor kappa beta (NF-Kβ) antagonists such as OT-551; hedgehog inhibitors such as CUR61414, cyclopamine, GDC-0449, or anti-hedgehog antibody; histone deacetylase (HDAC) inhibitors such as SAHA, PCI-24781, SB939, CHR-3996, CRA-024781, ITF2357, JNJ-26481585, or PCI-24781; retinoids such as isotretinoin; hepatocyte growth factor/scatter factor (HGF/SF) antagonist such as HGF/SF monoclonal antibody (e.g., AMG 102) or a c-Met kinase inhibitor such as crizotinib; synthetic bradykinin such as RMP-7; platelet-derived growth factor receptor inhibitors such as SU-101; anti-VEGF antibodies, including bevacizumab; and immune check point inhibitors including anti-CTLA-4 antibodies, anti-PD-1 antibodies, anti-PD-L1 antibodies, anti-TIM-3 antibodies and anti-LAG-3 antibodies.

In some embodiments, induction therapy comprising an anti-CTGF agent comprises the administration of a kinase inhibitor. In further embodiments, the kinase inhibitor is a tyrosine kinase inhibitor, serine kinase inhibitor or threonine kinase inhibitor. In additional embodiments, the kinase inhibitor is a Janus kinase inhibitor such as lestaurtinib or cyclin-dependent kinase inhibitor such as seliciclib. In other embodiments, the kinase inhibitor is selected from the group consisting of imatinib, dasatinib, nilotinib, gefitinib, sorafenib, sunitinib, lapatinib, dorafinib, sorafenib, sunitinib, vandetanib, pazopanib, vatalanib, AEE788, TG100801, SU5416 and SU6668.

Radiotherapy

In some embodiments, induction therapy comprising an anti-CTGF agent further comprises the administration of radiotherapy, before or after the administration of the anti-CTGF agent. Typically, radiation is administered from about 30 Gy to about 60 Gy in 1.8 Gy to 3 Gy fractions. For example, 10 fractions over 2 weeks (3 Gy per fraction), 25 fractions over 5 weeks (1.8 Gy per fraction) or 29 fractions over 6 weeks (1.8 Gy per fraction). Local boosts to the tumor bed are sometimes administered, for example, a 5.4-Gy boost. Radiotherapy can be administered by any acceptable means including split field, 3-D conformal radiotherapy or intensity modulation radiation therapy (IMRT). With IMRT, it is possible to first deliver doses of 45 to 50 Gy to larger RT fields and then deliver at total dose of 54 to 60 Gy to the tumor bed. Dose escalation to the tumor bed reduces the risk of local recurrence.

Chemoradiotherapy

As used herein, "chemoradiotherapy" is the concurrent administration of chemotherapy with radiotherapy. In the context of chemoradiotherapy, radiotherapy is typically administered in 1.8 Gy or 2.0 Gy fractions for a total dose of 45 Gy to 55.8 Gy. Concurrent chemotherapy usually comprises treatment with one or more of the following agents: capecitabine, cisplatin, docetaxel, 5-FU, gemcitabine, oxaliplatin, paclitaxel or streptozocin. Frequently, capecitabine is given at 800 to 900 mg/m$^2$ in divided doses twice daily on days when radiotherapy is administered. Treatment with cisplatin is usually intermittent, 20 mg/m$^2$ on days 1-5 during weeks 1 and 5. Gemcitabine is often administered at a dose of 300 to 400 mg/m$^2$ weekly. 5-FU is usually administered by continuous infusion or bolus injection at 200 mg/m$^2$ to 300 mg/m$^2$ daily. Chemotherapy administration can further be administered as a maintenance therapy for 1, 2, 3, 4, 5 or 6 cycles after radiotherapy.

Surgery

In some embodiments, the induction therapy comprising an anti-CTGF agent further comprises resection of the tumor. Typically, a Whipple operation (pancreaticoduodenectomy) is performed for a resectable tumor (LAPC) that is located in the head of the pancreas. Approximately, 80% of all adenocarcinomas of the pancreas occur in the head of the pancreas. A standard Whipple operation entails resection of the head of the pancreas, the bottom half of the bile duct, the duodenum and part of the stomach. In the pylorus preserving Whipple operation, the stomach is preserved.

Subjects with resectable LAPC of the body and tail of the pancreas are usually treated with a distal pancreatectomy and frequently splenectomy. As required, subjects with resectable LAPC may also undergo total pancreatectomy.

Treatment and Effective Amount

As used herein, the term "effective amount" in the context of administering an induction therapy comprising an anti-CTGF agent to a subject with pancreatic cancer, is an amount sufficient to prevent the continued growth of the tumor, i.e., stabilize the disease; cause a reduction in tumor volume, metabolic rate or viability; or reduce the spread or viability of metastases. Frequently, monitoring the growth rate of pancreatic cancer and its response to therapy is assessed using the Response Evaluation Criteria in Solid Tumors (RECIST) criteria. In specific embodiments, an effective amount of an induction therapy comprising an anti-CTGF agent is capable of at least stabilizing the disease in at least about 10%, 20%, 25%, 30%, 35%, 40%, 45%, 50%, 55%, 60%, 65%, 70%, 75%, 80%, 85%, or 90% of patients with PC. In particular embodiments, the tumor stabilization is maintained for at least 1, 2, 3, 4, 5, 6, 8 or 10 months following completion of induction therapy.

In other embodiments, an effective amount of an induction therapy comprising an anti-CTGF agent produces a partial response (PR) or complete response (CR), as determined by RECIST criteria, in at least about 10%, 20%, 25%, 30%, 35%, 40%, 45%, 50%, 55%, 60%, 65%, 70%, 75%, 80%, 85%, or 90% of patients with PC. In particular embodiments, the disease regression is maintained for at least 1, 2, 3, 4, 5, 6, 8 or 10 months following completion of induction therapy.

In further embodiments, an effective amount of an induction therapy comprising an anti-CTGF agent produces a reduction in a tumor marker of at least 10%, 20%, 30%, 40%, 50%, 60%, 70%, 80%, 90% or 95% compared to a baseline measurement. Useful tumor markers include carcinoembryonic antigen (CEA), carbohydrate antigen 19-9 (CA19-9), UL16 binding protein 2 (ULBP2), carcinoembryonic antigen-related cell adhesion molecule 1 (CEACAM1), MUC1, alpha-fetoprotein, apolipoprotein C-I (ApoC-I), apolipoprotein A-II (ApoA-II), pancreatic associated antigen (Span-1), CA50 antigen, DU-PAN-2, serum amyloid A, insulin-like growth factor-binding protein-1a (IGEBP-1a), M2-pyruvate kinase, alpha4GnT, NPC-1C, elastase-1, tissue polypeptide antigen (TPA), tissue polypeptide-specific antigen (TPS) and combinations thereof. In particular embodiments, the tumor marker is CA19-9. In other embodiments, a combination of tumor markers comprising CA19-9, DU-PAN-2 and Span-1 is used.

In other embodiments, an effective amount of an induction therapy comprising an anti-CTGF agent produces a reduction in FDG-PET $SUV_{max}$ of at least 10%, 20%, 25%, 30%, 35%, 40%, 45%, 50%, 55%, 60%, 65%, 70%, 75%, 80%, 85%, 90% or 95% compared to a baseline measurement.

In other embodiments, an effective amount of an induction therapy comprising an anti-CTGF agent converts (downstages) an unresectable LAPC to borderline resectable or resectable status; or converts (downstages) a borderline resectable LAPC to resectable tumor status. In some embodiments, the administration of an effective amount of an induction therapy comprising an anti-CTGF agent converts at least about 10%, 20%, 25%, 30%, 35%, 40%, 45%, 50%, 55%, 60%, 65%, 70%, 75%, 80%, 85%, or 90% of unresectable LAPCs into at least borderline resectable status. In other embodiments, the administration of an effective amount of an induction therapy comprising an anti-CTGF converts at least about 10%, 20%, 25%, 30%, 35%, 40%, 45%, 50%, 55%, 60%, 65%, 70%, 75%, 80%, 85%, or 90% of borderline resectable LAPCs into resectable status.

In other embodiments, the administration of an effective amount of an induction therapy comprising an anti-CTGF agent produces R0 resections in at least about 10%, 20%, 25%, 30%, 35%, 40%, 45%, 50%, 55%, 60%, 65%, 70%, 75%, 80%, 85%, or 90% of subjects that present with unresectable or borderline resectable LAPC.

In some embodiments, an effective amount of an induction therapy comprising an anti-CTGF agent synergizes with radiotherapy providing an alternate means to convert an unresectable LAPC to at least a borderline LAPC or convert a borderline resectable LAPC to a resectable LAPC. Radiotherapy can be administered to any standard total radiation dose, e.g., 45 Gy to 52.2 Gy, using any conventional means.

In some embodiments, an effective amount of an induction therapy comprising an anti-CTGF agent sensitizes or resensitizes a subject with PC to radiotherapy. In some embodiments, induction therapy comprising an anti-CTGF agent is administered in conjunction with standard radiotherapy, e.g., 50.4 Gy in 28 fractions. A sensitizing amount of an induction therapy comprising an anti-CTGF agent can be administered to a patient in combination with radiotherapy or within 1 day, within 2 days, within 3 days, within 4 days, within 5 days, within 6 days, within 1 week, within 2 weeks or within 1 month of radiotherapy.

In some embodiments, an effective amount of an induction therapy comprising an anti-CTGF agent increases disease-free survival, progression-free survival or overall survival in PC patients compared to historical controls, including current standard of care therapy. Typically, survival values can be determined using Kaplan-Meier plots or other suitable means. In further embodiments, the survival is extended at least 1 month, 2 months, 3 months, 4 months, 5 months, 6 months, 7 months, 8 months, 9 months, 10 months, 11 months, 12 months, 15 months, 18 months or 24 months beyond historical controls, including current standard of care therapy. In other embodiments, an effective amount of an induction therapy comprising an anti-CTGF agent increases the survival of subjects with PC, including subjects with unresectable, borderline resectable or resectable LAPC, by at least 10%, 20%, 30%, 40%, 50%, 60%, 70%, 80%, 90% or 100% compared to a control group or historical controls, including current standard of care therapy. In additional embodiments, an effective amount of an induction therapy comprising an anti-CTGF agent produces a disease-free survival, progression-free survival or overall survival rate of at least 6 months, 7 months, 8 months, 9 months, 10 months, 11 months, 12 months, 13 months, 14 months, 15 months, 16 months, 17 months, 18 months, 19 months, 20 months, 21 months, 22 months, 23 months, 24 months, 28 months, 32 months, 36 months or 40 months. In other embodiments, an effective amount of an induction therapy comprising an anti-CTGF agent produces a 1-year survival rate of subjects with PC of at least 10%, at least 20%, at least 30%, at least 40%, at least 50%, at least 60%, at least 70%, at least 80% or at least 90%. In further embodiments, an effective amount of an induction therapy comprising an anti-CTGF agent produces a 3-year survival rate of subjects with PC of at least 10%, at least 15%, at least 20%, at least 25%, at least 30%, at least 35%, at least 40%, at least 45%, at least 50%, at least 55% or at least 60%.

In some embodiments, an effective amount of an induction therapy comprising an anti-CTGF agent increases time to tumor progression (TTP) compared to historical controls, including current standard of care therapy, by at least about 1 month, 2 months, 3 months, 4 months, 5 months, 6 months, 7 months, 8 months, 9 months, 10 months, 11 months, 12 months, 15 months, 18 months or 24 months.

In other embodiments, an effective amount of an induction therapy comprising an anti-CTGF agent reduces one or more symptoms of PC including pain and gastric outlet obstruction. In further embodiments, an effective amount of induction therapy comprising anti-CTGF agent obviates the need for gastrojejenostomy and/or biliary bypass surgery.

In some embodiments, an effective amount of induction therapy comprising an anti-CTGF agent prevents or controls metastatic disease including distant metastases. In additional embodiments, an effective amount of an induction therapy comprising an anti-CTGF agent is administered after a main therapy, for example, surgery or radiotherapy, to prevent or control metastatic disease including distant metastases. In other embodiments, an effective amount of an induction therapy comprising an anti-CTGF agent is administered for palliation of a pancreatic cancer symptom. In further embodiments, palliation is achieved for at least one symptom of pancreatic cancer selected from the list consisting of anorexia, abdominal discomfort, binary obstruction, diabetes, jaundice, fatigue, fever, intestinal obstruction, malaise, pain, pruritus and weight loss.

In additional embodiments, an effective amount of an induction therapy comprising an anti-CTGF antibody comprises the administration of at least about 1 mg/kg, 5 mg/kg, 10 mg/kg, 15 mg/kg, 17.5 mg/kg, 20 mg/kg, 22.5 mg/kg, 25 mg/kg, 30 mg/kg, 35 mg/kg, 40 mg/kg, 45 mg/kg, 50 mg/kg, 60 mg/kg, 80 mg/kg, 100 mg/kg, 120 mg/kg or 150 mg/kg of an anti-CTGF antibody. In other embodiments, an effective amount of an induction therapy comprising an anti-CTGF antibody comprises the administration of not more than about 15 mg/kg, 20 mg/kg, 25 mg/kg, 30 mg/kg, 35 mg/kg, 40 mg/kg, 45 mg/kg, 50 mg/kg, 60 mg/kg, 80 mg/kg or 100 mg/kg of an anti-CTGF antibody. In further embodiments, an effective amount of an induction therapy comprising an anti-CTGF antibody comprises the administration of between about 1 mg/kg to 150 mg/kg, 5 mg/kg to 100 mg/kg, 10 mg/kg to 80 mg/kg, 15 mg/kg to 60 mg/kg, 20 mg/kg to 60 mg/kg, 30 mg/kg to 75 mg/kg or 35 mg/kg to 50 mg/kg. In other embodiments, an effective amount of an induction therapy comprising an anti-CTGF antibody comprises the administration of about 15 mg/kg, 17.5 mg/kg, 20 mg/kg, 22.5 mg/kg, 25 mg/kg, 30 mg/kg, 35 mg/kg, 45 mg/kg, 50 mg/kg or 60 mg/kg of an anti-CTGF antibody.

In further embodiments, the anti-CTGF antibody is initially administered as a loading dose. As used herein, the term "loading dose" refers to an antibody dose used to rapidly achieve a desired antibody target level, typically, a target steady-state antibody level or an antibody level that correlates with a desired pharmacological or clinical response. A loading dose can be administered as a single injection or infusion, or alternatively, the loading dose can be administered as multiple antibody injections or infusion within an initial treatment period or cycle, e.g., three infusions of 15 mg/kg spaced over 3 days for a total infusion of 45 mg/kg or an extra infusion interspursed between two standard infusions, for instance, an infusion of 35 mg/kg administered on Day 8 of the first 28 day treatment cycle that has standard infusions of 35 mg/kg fixed at Day 1 and Day 15 of the treatment cycle. In particular embodiments, the loading dose is at least about 15 mg/kg, 20 mg/kg, 22.5 mg/kg, 25 mg/kg, 30 mg/kg, 35 mg/kg, 40 mg/kg, 45 mg/kg, 50 mg/kg, 55 mg/kg, 60 mg/kg, 70 mg/kg, 80 mg/kg, 100 mg/kg, 105 mg/kg or 120 mg/kg. In specific embodiments, the loading dose is about 15 mg/kg, 20 mg/kg, 25 mg/kg, 30 mg/kg, 35 mg/kg, 45 mg/kg, 55 mg/kg, 60 mg/kg, 75 mg/kg, 90 mg/kg, 105 mg/kg or 120 mg/kg.

In some embodiments, the loading dose is the antibody dose that is sufficient to achieve an antibody concentration in blood of at least about 100 µg/ml, 125 µg/ml, 150 µg/ml, 200 µg/ml, 300 µg/ml, 400 µg/ml or 500 µg/ml when measured at the end of the treatment cycle ($C_{mm}$). In specific embodiments, the loading dose is the antibody dose sufficient to achieve an antibody blood concentration of at least about 150 µg/ml when measured about 14 days post-administration, i.e., at the end of a 2 week treatment cycle, or at the end of a 4 week treatment cycle, wherein a second antibody dose is administered on day 15 of the treatment cycle.

In other embodiments, the loading dose achieves an antibody concentration that is sufficient to inhibit or reduce tumor cell growth, tumor cell motility, tumor cell invasiveness, or tumor cell metabolism. In additional embodiments, the antibody concentration achieved with the loading dose correlates with a reduction in tumor size or volume, or a reduction in the level of a tumor marker compared to a baseline measurement.

In further embodiment, the antibody concentration achieved with the loading dose correlates with a clinical response, including, for example, a reduction or amelioration of anorexia, weight loss, fatigue, jaundice, pain, including abdominal pain, analgesic or narcotic consumption, nausea, indigestion, diarrhea, bloating, malaise, itching, dehydration or hyperglycemia.

In further embodiments of the induction therapy, one or more maintenance doses of an anti-CTGF antibody are administered after a loading dose. The term "maintenance dose" as used herein refers to an antibody dose sufficient to maintain a desired antibody concentration in blood that was achieved with the loading dose. Typically, an antibody maintenance dose is used to maintain a desired pharmacologic or clinical response that was achieved with the loading dose. Usually, the maintenance dose is a less than the loading dose, but it can be the same amount or a higher amount than as the loading dose. In some embodiments, the maintenance dose is at least 15 mg/kg, 20 mg/kg, 22.5 mg/kg, 25 mg/kg, 30 mg/kg, 35 mg/kg, 40 mg/kg, 45 mg/kg, 50 mg/kg, 55 mg/kg, 75 mg/kg or 100 mg/kg. In specific embodiments, the maintenance dose is about 15 mg/kg, 17.5 mg/kg, 22.5 mg/kg, 25 mg/kg, 35 mg/kg 45 mg/kg or 55 mg/kg. In specific embodiments, the maintenance dose is 35 mg/kg administered on Days 1 and 15 of a 28 day treatment cycle.

In some embodiments, the amount of anti-CTGF antibody administered to a patient is based on titration. The term "titration," as used herein, means the incremental increase or decrease in antibody dosage until a target antibody concentration in a patient sample, typically, blood, is achieved, or a desired pharmacologic or clinical response is observed.

Antibody titration based on a target antibody concentration can be accomplished in an iterative manner as illustrated in the following example based on increasing the antibody dose as needed to achieve a desired antibody concentration in a patient sample. Antibody titration is performed by administering a first anti-CTGF antibody dose, measuring the antibody concentration in a first patient sample to obtain a first patient antibody concentration and comparing the first patient antibody concentration to a first target antibody concentration. If the first patient antibody concentration equals or exceeds the first target antibody concentration, then the patient receives the same amount of anti-CTGF antibody in a second antibody dose. Optionally, a second patient sample can be obtained and assayed for a second patient antibody concentration that is compared to the first target antibody concentration so that a further dose adjustment can be made if desired.

If the first patient antibody concentration is below the first target antibody concentration, then a larger amount of anti-CTGF antibody is administered in the second antibody dose. Typically, the second antibody dose is calculated to produce a second patient antibody concentration that equals or exceeds the first target antibody concentration. Following the administration of the second antibody dose, a second patient sample is measured to obtain a second patient antibody concentration that is compared to the first target antibody concentration. If the second patient antibody concentration equals or exceeds the first target antibody concentration, then the patient receives the same amount of anti-CTGF antibody in a third antibody dose. If the second patient antibody concentration was below the first target antibody concentration, then a larger amount of anti-CTGF antibody is administered in a third anti-CTGF antibody dose. The titration of the antibody dose can be continued until the desire antibody concentration is achieved. Typically, the patient samples are obtained at about the same time point post the respective antibody administration using identical samples, e.g., blood samples.

In some embodiments, the first target antibody concentration is at least about 1 µg/ml, 10 µg/ml, 25 µg/ml, 50 µg/ml, 75 µg/ml, 100 µg/ml, 125 µg/ml, 150 µg/ml, 200 µg/ml, 300 µg/ml, 400 µg/ml or 500 µg/ml. In other embodiments, the first target antibody concentration is not more than about 10 µg/ml, 25 µg/ml, 50 µg/ml, 75 µg/ml, 100 µg/ml, 125 µg/ml, 150 µg/ml, 200 µg/ml, 300 µg/ml, 400 µg/ml or 500 µg/ml. In particular embodiments, the first target antibody concentration is at least about 150 µg/ml.

When the antibody is titrated based on a desired antibody concentration in a patient sample, the patient sample is usually obtained at or near the end of a treatment cycle. Usually, the antibody $C_{min}$ is calculated. Typically, the antibody concentration is measured at about 2, 3, 4, 5, 6, 7, 8, 9, 10, 11, 12, 13, 14, 15, 16, 17, 18, 19, 20, 21, 24 or 28 days post antibody administration.

Alternately, antibody titration can be based on the intent to achieve a desired pharmacologic or clinical response (endpoint). For example, a first anti-CTGF antibody dose is administered to a patient and then the patient is examined to at an appropriate time period to see if a desired pharmacologic or clinical response was produced. If the first anti-CTGF antibody dose produced the desired pharmacologic or clinical response, then the same amount of anti-CTGF antibody is administered in the second and subsequent doses. On the other hand, if the first anti-CTGF antibody dose did not produce the desired pharmacologic or clinical response, than the amount of anti-CTGF antibody administered in a second antibody dose is increased. The patient is again examined at the appropriate time period to see if the second antibody dose produced the desired pharmacologic or clinical response. If the second anti-CTGF antibody dose produced the desired pharmacologic or clinical response, the same amount of anti-CTGF antibody is administered in the third and subsequent doses. If the desired pharmacologic or clinical response is not observed, then the amount of antibody administered in the third anti-CTGF dose is increased above the amount that was administered in the second antibody dose and the patient is observed at the appropriate time to see of the desired pharmacologic or clinical response was produced. If the third anti-CTGF antibody dose produced the desired pharmacologic or clinical response, then the same amount of anti-CTGF antibody is administered in the fourth and subsequent doses. If not, than the antibody dose escalation continues in the manner illustrated above.

Typically, pharmacological response endpoints for antibody titration include, for example, a reduction in tumor size or volume, a reduction in tumor metabolism or a reduction in a tumor marker concentration. Clinical response endpoints include, for example, a reduction or amelioration of anorexia, weight loss, fatigue, jaundice, pain, including abdominal pain, analgesic or narcotic consumption, nausea, indigestion, diarrhea, bloating, malaise, itching, dehydration or hyperglycemia.

Antibody titration ensures that during the treatment course patients are administered an antibody dose that either achieves or exceeds a desired target antibody concentration or produces a desired pharmacologic or clinical response. Titration accounts for the patient-specific differences in various factors such as quantity and accessibility of antigen, degree of tumor burden, degree of tumor desmoplasia, rate of antibody catabolism and antibody half-life in addition to other patient-specific factors such as age, gender, other concurrent medical conditions and degree of renal sufficiency. Typically, the patient sample is a blood sample, but other biologic samples are contemplated such as serous fluids from the peritoneal cavity, lungs, or heart; or cerebrospinal fluid; or a tissue or tumor biopsy or other surgical sample.

In other embodiments, the anti-CTGF agent is an anti-CTGF oligonucleotide wherein an effective amount of an induction therapy comprises the administration of 0.1 mg to 10,000 mg, from 1 mg to 5,000 mg, from 10 mg to 2,500 mg, from 50 mg to 1,000 mg, from 100 mg to 500 mg, from 100 mg to 1,000 mg, from 250 mg to 1,000 mg or from 500 mg to 2,500 mg of the anti-CTGF oligonucleotide.

In some embodiments, induction therapy comprising an anti-CTGF agent comprises the administration of one or more additional therapeutic agents. In other embodiments, the additional therapeutic agent is administered at a range from about 0.1 mg to about 10,000 mg, from about 1 mg to about 5,000 mg, from about 10 mg to about 2,500 mg, from about 50 mg to about 1,000 mg, from about 100 mg to about 500 mg, from about 100 mg to about 1,000 mg, from about 250 mg to about 1,000 mg or from about 500 mg to about 2,500 mg. In further embodiments, the additional therapeutic agent is a chemotherapy agent. In additional embodiments, the chemotherapy agent is selected from the group consisting of antimetabolites, mitotic inhibitors, topisomerase inhibitors, alkylating agents, anti-tumor antibiotics, differentiating agents and hormones. Typically, the chemotherapy agent used in induction therapy is administered at a standard dosage used in the conventional treatment of pancreatic cancer. For instance, gemcitabine is usually administered at a dose of about 1,000 mg/m$^2$.

Induction therapy comprising an anti-CTGF agent can be administered to subjects with PC as often as required, e.g., once a day, every other day, once or twice per week, biweekly or monthly. In some embodiments, the individual components of an induction therapy comprising an anti-CTGF agent, e.g., anti-CTGF agent, antimetabolite and mitotic inhibitor, are administered simultaneously, i.e., same day, for example on the first day of a treatment cycle. In other embodiments, the individual components of an induction therapy comprising an anti-CTGF agent are administered sequentially, for example, on alternate days. In further embodiments, the individual components of an induction therapy comprising an anti-CTGF agent are administered using separate administration schedules that may be overlapping or concurrent. For example, the anti-CTGF agent can be administered at the beginning and about the middle of a treatment cycle, while an antimetabolite and a mitotic inhibitor can be administered at the beginning, at about the first quarter and about the middle of a treatment cycle. As a specific example, using a 28 day treatment cycle, an anti-CTGF agent can be administered on Day 1 and Day 15, while an antimetabolite and a mitotic inhibitor can be administered on Day 1, Day 8 and Day 15.

In particular embodiments, an effective amount of an induction therapy comprising an anti-CTGF agent comprises the administration of an anti-CTGF antibody at a dose of about 35 mg/kg, the administration of gemcitabine at a dose of about 1,000 mg/m$^2$ and the administration of nab-paclitaxel at a dose of about 125 mg/m$^2$. In further embodiments, the anti-CTGF antibody is administered on Day 1 and Day 15 of a 28 day treatment cycle. In additional embodiments, gemcitabine is administered on Day 1, Day 8 and Day 15 of a 28 day treatment cycle. In still further embodiments, the nab-paclitaxel is administered on Day 1, Day 8 and Day 15 of a 28 day treatment cycle.

In some embodiments, the conversion of an unresectable LAPC to at least borderline resectable status or the conversion of a borderline resectable LAPC to a resectable status is achieved within 1, 2, 3, 4, 5, 6, 7, 8, 10, 12 or 16 induction therapy treatment cycles. In other embodiments, the conversion of unresectable LAPC to at least borderline resectable status or the conversion of a borderline resectable LAPC to a resectable status is achieved in 4 weeks or less, 8 weeks or less, 12 weeks or less, 18 weeks or less, 24 weeks or less, 28 weeks or less, 32 weeks or less, 40 weeks or less, or 48 weeks or less from the start of induction therapy comprising an effective amount of an anti-CTGF agent.

Subjects Suitable for Treatment with an Induction Therapy Comprising an Anti-CTGF Agent The methods of the invention are suitable for the treatment of subjects diagnosed with PC, including subjects diagnosed with unresectable, borderline resectable or resectable LAPC. Diagnosis can be performed using any diagnostic method recognized in the art including CAT scan, X-ray, PET scan, single photon emission computed tomography (SPECT scan), ultrasound, including endoscopic sonography, magnetic resonance imaging (MRI), magnetic resonance cholangiopancreatography, laparoscopic examination, histopathology or any combination thereof.

In some embodiments, the PC patients to be treated with an induction therapy comprising an anti-CTGF agent are treatment naïve and may be newly diagnosed with PC. In further embodiments, the subjects with PC are "unresponsive to conventional treatment," including unresponsive to conventional induction therapy, chemotherapy, chemoradiotherapy or radiotherapy. In still further embodiments, the PC patients treated with an induction therapy comprising an anti-CTGF agent have relapsed with localized tumor recurrence after initially responding and completing conventional induction therapy or chemotherapy and/or tumor resection. In additional embodiments, the PC patients treated with an induction therapy comprising an anti-CTGF agent have previously achieved only partial resection of their tumors. In other embodiments, the PC patients treated with an induction therapy comprising an anti-CTGF agent may initially have responded to conventional induction therapy or chemotherapy, but became resistant to conventional induction therapy or chemotherapy prior to the end of the treatment course. In certain embodiments, suitable patients are those patients whose tumors over-express SPARC.

The disclosed methods are suitable for treating all forms of PCs including acinar cell carcinomas, adenocarcinomas, adenosquamous carcinomas, ampullary cancers, colloid carcinomas, giant cell tumors, hepatoid carcinomas, intraductal papillary-mucinous neoplasms, mucinous cystadenocarcinomas, pancreatoblastomas, serous cystadenocarcinomas, signet ring cell carcinomas, solid and pseudopapillary tumors, undifferentiated carcinomas, gastrinomas, glucagonomas, insulinomas, nonfunctional islet cell tumors, somatostatinomas and vasoactive intestinal peptide-releasing tumors. The disease can originate in any part of the pancrease, e.g., the head, uncinate process, body or tail. In particular embodiments, the PC is an adenocarcinoma. In further embodiments, the adenocarcinoma is ductal adenocarcinoma.

Suitable patients further include patients with ECOG performance status of 0-3. Additionally, patients with biliary stents are also suitable for treatment using the methods of the invention.

Pharmaceutical Formulations and Routes of Administration

The compositions and compounds suitable for use in the methods of the present invention can be delivered directly or in pharmaceutical compositions containing excipients, as is well known in the art. Various formulations and drug delivery systems are available in the art and depend in part on the intended route of administration. (See, e.g., Gennaro, ed. (2000) *Remington's Pharmaceutical Sciences*, supra; and Hardman, Limbird, and Gilman, eds. (2001) *The Pharmacological Basis of Therapeutics*, supra.)

Suitable routes of administration may, for example, include oral, rectal, topical, nasal, pulmonary, ocular, intestinal, and parenteral administration. Primary routes for parenteral administration include intravenous, intramuscular, and subcutaneous administration. Secondary routes of administration include intraperitoneal, intra-arterial, and intralesional administration.

Pharmaceutical dosage forms of a suitable compound for use in the invention may be provided in an instant release, controlled release, sustained release, or target drug-delivery system. Commonly used dosage forms include, for example, solutions and suspensions, (micro-) emulsions, ointments, gels and patches, liposomes, tablets, dragees, soft or hard shell capsules, suppositories, ovules, implants, amorphous or crystalline powders, aerosols, and lyophilized formulations. Depending on route of administration used, special devices may be required for application or administration of the drug, such as, for example, syringes and needles, inhalers, pumps, injection pens, applicators, or special flasks. Pharmaceutical dosage forms are often composed of the drug, an excipient(s), and a container/closure system. One or multiple excipients, also referred to as inactive ingredients, can be added to a compound of the invention to improve or facilitate manufacturing, stability, administration, and safety of the drug, and can provide a means to achieve a desired drug release profile. Therefore, the type of excipient(s) to be added to the drug can depend on various factors, such as, for example, the physical and chemical properties of the drug, the route of administration, and the manufacturing procedure. Pharmaceutically acceptable excipients are available in the art, and include those listed in various pharmacopoeias. (See, e.g., USP, JP, EP, and BP), Inactive Ingredient Guide available through the FDA's website, and *Handbook of Pharmaceutical Additives*, ed. Ash; Synapse Information Resources, Inc. 2002.)

Pharmaceutical dosage forms of a compound for use in the present invention may be manufactured by any of the methods well-known in the art, such as, for example, by conventional mixing, sieving, dissolving, melting, granulating, dragee-making, tabletting, suspending, extruding, spray-drying, levigating, emulsifying, (nano/micro-) encapsulating, entrapping, or lyophilization processes. As noted above, the compositions for use in the present invention can include one or more physiologically acceptable inactive ingredients that facilitate processing of active molecules into preparations for pharmaceutical use.

Proper formulation is dependent upon the desired route of administration. For intravenous injection, for example, the composition may be formulated in aqueous solution, if necessary, using physiologically compatible buffers, including, for example, phosphate, histidine, or citrate for adjustment of the formulation pH, and a tonicity agent, such as, for example, sodium chloride or dextrose. For transmucosal or nasal administration, semisolid, liquid formulations, or patches may be preferred, possibly containing penetration enhancers. Such penetrants are generally known in the art. For oral administration, the compounds can be formulated in liquid or solid dosage forms and as instant or controlled/sustained release formulations. Suitable dosage forms for oral ingestion by a subject include tablets, pills, dragees, hard and soft shell capsules, liquids, gels, syrups, slurries, suspensions, and emulsions. The compounds may also be formulated in rectal compositions, such as suppositories or retention enemas, e.g., containing conventional suppository bases such as cocoa butter or other glycerides.

Solid oral dosage forms can be obtained using excipients, which may include, fillers, disintegrants, binders (dry and wet), dissolution retardants, lubricants, glidants, antiadherants, cationic exchange resins, wetting agents, antioxidants, preservatives, coloring, and flavoring agents. These excipients can be of synthetic or natural source. Examples of such excipients include cellulose derivatives, citric acid, dicalcium phosphate, gelatine, magnesium carbonate, magnesium/sodium lauryl sulfate, mannitol, polyethylene glycol, polyvinyl pyrrolidone, silicates, silicium dioxide, sodium benzoate, sorbitol, starches, stearic acid or a salt thereof, sugars (i.e. dextrose, sucrose, lactose, etc.), talc, tragacanth mucilage, vegetable oils (hydrogenated), and waxes. Ethanol and water may serve as granulation aides. In certain instances, coating of tablets with, for example, a taste-masking film, a stomach acid resistant film, or a release-retarding film is desirable. Natural and synthetic polymers, in combination with colorants, sugars, and organic solvents or water, are often used to coat tablets, resulting in dragees. When a capsule is preferred over a tablet, the drug powder, suspension, or solution thereof can be delivered in a compatible hard or soft shell capsule.

Compositions formulated for parenteral administration by injection are usually sterile and, can be presented in unit dosage forms, e.g., in ampoules, syringes, injection pens, or in multi-dose containers, the latter usually containing a preservative. The compositions may take such forms as suspensions, solutions, or emulsions in oily or aqueous vehicles, and may contain formulatory agents, such as buffers, tonicity agents, viscosity enhancing agents, surfactants, suspending and dispersing agents, antioxidants, biocompatible polymers, chelating agents, and preservatives. Depending on the injection site, the vehicle may contain water, a synthetic or vegetable oil, and/or organic co-solvents. In certain instances, such as with a lyophilized product or a concentrate, the parenteral formulation would be reconstituted or diluted prior to administration. Depot formulations, providing controlled or sustained release of a compound of the invention, may include injectable suspensions of nano/micro particles or nano/micro or non-micronized crystals. Polymers such as poly(lactic acid), poly(glycolic acid), or copolymers thereof, can serve as controlled/sustained release matrices, in addition to others well known in the art. Other depot delivery systems may be presented in form of implants and pumps requiring incision.

Suitable carriers for intravenous injection for the molecules of the invention are well-known in the art and include water-based solutions containing a base, such as, for example, sodium hydroxide, to form an ionized compound, sucrose or sodium chloride as a tonicity agent, for example, the buffer contains phosphate or histidine. Co-solvents, such as, for example, polyethylene glycols, may be added. These water-based systems are effective at dissolving compounds of the invention and produce low toxicity upon systemic administration. The proportions of the components of a solution system may be varied considerably, without destroying solubility and toxicity characteristics. Furthermore, the identity of the components may be varied. For example, low-toxicity surfactants, such as polysorbates or poloxamers, may be used, as can polyethylene glycol or other co-solvents, biocompatible polymers such as polyvinyl pyrrolidone may be added, and other sugars and polyols may substitute for dextrose.

Anti-CTGF antibody formulations for use in accordance with the present invention may be prepared by mixing an anti-CTGF antibody with pharmaceutically acceptable carriers, excipients or stabilizers that are nontoxic to recipients at the dosages and concentrations employed. Anti-CTGF antibody formulations may include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); carriers; hydrophilic polymers such as polyvinylpyrrolidone; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes; and/or non-ionic surfactants or polyethylene glycol.

In particular, anti-CTGF antibody formulations may further comprise low molecular weight polypeptides; carriers such as serum albumin, gelatin, or immunoglobulins; and amino acids such as glycine, glutamine, asparagine, histidine, arginine, or lysine. The anti-CTGF antibody formulations can be lyophilized as described in PCT/US1996/012251. Additionally, sustained-release preparations may also be prepared. Frequently, polymers such as poly(lactic acid), poly(glycolic acid), or copolymers thereof serve as controlled/sustained release matrices, in addition to others well known in the art.

The anti-CTGF antibodies can be supplied or administered at any desired concentration. In some embodiments, the anti-CTGF antibody concentration is at least 1 mg/ml, 5 mg/ml, 10 mg/ml, 20 mg/ml, 25 mg/ml, 50 mg/ml, 75 mg/ml, 100 mg/ml, 125 mg/ml, 150 mg/ml, or 200 mg/ml. In other embodiments, the anti-CTGF antibody concentration is no more than about 5 mg/ml, 10 mg/ml, 20 mg/ml, 25 mg/ml, 50 mg/ml, 75 mg/ml, 100 mg/ml, 125 mg/ml, 150 mg/ml, 200 mg/ml, 250 mg/ml, or 300 mg/ml. In further embodiments, the anti-CTGF antibody concentration is between 5 mg/ml to 20 mg/ml, 20 mg/ml to 50 mg/ml, 50 mg/ml to 100 mg/ml, 100 mg/ml to 200 mg/ml, or 200 mg/ml to 300 mg/ml.

Articles of Manufacture

The present compositions may, if desired, be presented in a pack or dispenser device containing one or more unit dosage forms comprising an anti-CTGF agent. Such a pack or device may, for example, comprise metal or plastic foil, such as a blister pack, or glass and rubber stoppers such as in vials. The container containing an anti-CTGF agent or composition may have a sterile access port (for example the container may be an intravenous solution bag or a vial having a stopper pierceable by a hypodermic injection needle). The article of manufacture may further comprise an additional container comprising a pharmaceutically acceptable diluent buffer, such as bacteriostatic water for injection (BWFI), phosphate-buffered saline, Ringer's solution, and/or dextrose solution. The article of manufacture may further include other materials desirable from a commercial and user standpoint, including other buffers, diluents, filters, needles, and syringes. Compositions comprising an anti-CTGF agent formulated in a compatible pharmaceutical carrier may also be prepared, placed in an appropriate container, and labeled for treatment of PC. The pack or dispenser device may further be accompanied by instructions for administration.

The pack or dispenser may also be accompanied by additional packs or dispensers containing one or more other therapeutic agent such as an antimetabolite and/or a mitotic inhibitor. Additionally, instructions for administration of the other therapeutic agent may further be provided.

These and other embodiments of the present invention will readily occur to those of ordinary skill in the art in view of the disclosure herein.

EXAMPLES

The invention is further understood by reference to the following examples, which are intended to be purely exemplary of the invention. The present invention is not limited in scope by the exemplified embodiments, which are intended as illustrations of single aspects of the invention only. Any methods that are functionally equivalent are within the scope of the invention. Various modifications of the invention in addition to those described herein will become apparent to those skilled in the art from the foregoing description and accompanying figures. Such modifications fall within the scope of the appended claims.

Example 1

A Phase-1, open-label study is performed on 15 LAPC patients with unresectable disease. During an initial screening period, all patients are laproscopically staged and their tumor biopsied. Patients with no evidence of metastatic disease and having an unresectable tumor mass that appears to offer the potential to be converted (downstaged) to at least borderline resectable status are classified as eligible. Eligible patients receive up to six, 28-day cycles of induction therapy comprising the anti-CTGF antibody FG-3019, an antibody that is identical to CLN-1. The induction therapy also comprises an antimetabolite (gemcitabine) and a mitotic inhibitor (nab-paclitaxel). Following the completion of induction therapy, patients are laproscopically restaged and their tumor biopsied. Patients that achieve at least "borderline" resectable LAPC status have their tumor resected. They are then followed for time to tumor progression (TTP) and overall survival (OS). Patients with disease progression after 6 or fewer cycles of induction therapy have treatment discontinued. A schematic overview of the study is provided in FIG. 1. The end of study (EOS) is defined as 28 days after the last dose of FG-3019. The primary efficacy endpoint is the proportion of subjects in whom R0 resection is achieved following induction therapy.

FG-3019 is administered on Day 1 and Day 15 of each cycle at a dose of 30 mg/kg by IV infusion. Gemcitabine, 1000 mg/m$^2$, and nab-paclitaxel, 125 mg/m$^2$, are administered on Day 1, 8 and 15 of each cycle following label instructions. Patients may be treated for up to 6 cycles.

Subjects who are not eligible for tumor resection are offered alternate therapy including other chemotherapy, chemoradiotherapy or radiotherapy and are then followed to collect TTP and OS data. For both eligible and ineligible patients, TTP is defined as a time frame from date of study entry until date of clinical and/or radiological progression, assessed up to 5 years. OS is defined as a time from a date of study entry until date of death, assessed up to 5 years.

Example 2

A Phase 2, randomized, open-label trial is performed to evaluate safety and tolerability of gemcitabine plus Nab-paclitaxel with the anti-CTGF antibody, FG-3019, (Arm A) compared to gemcitabine plus Nab-paclitaxel (Arm B) in subjects with locally advanced, unresectable pancreatic cancer. Up to 40 evaluable subjects are included in this trial.

Figure 2:
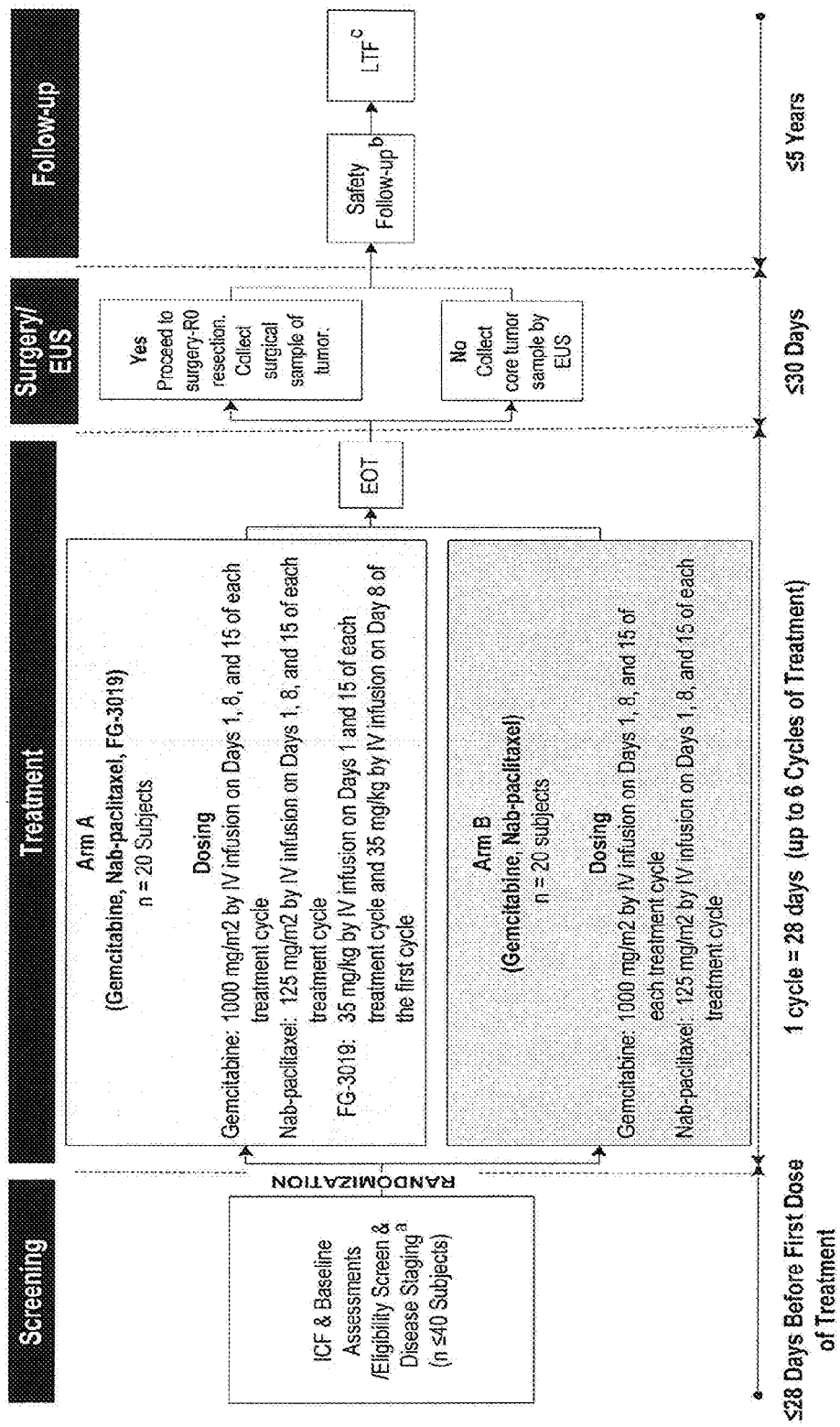
FIG. 2 is a schematic overview of the study design for a Phase 2, randomized, open-label study of gemcitabine and nab-paclitaxel with or without the anti-CTGF antibody, FG-3019, as induction therapy in subjects with unresectable LAPC. Each induction therapy cycle is 28 days in length. Abbreviations: ICF=informed consent form; EOT=end of treatment; EUS=endoscopic ultrasound; and LTF=long-term follow-up. [a]Includes laparoscopic staging and core biopsy. [b]Safety follow-up of 28 days following the last dose of study drug or 30 days following discharge after surgery. [c]Up to 5 years follow-up for progression and survival.

The trial has four stages: 1) screening and disease staging; 2) induction therapy; 3) surgery or short-term follow up; and 4) long-term follow up. A schematic overview of the study, including study period timeframes, is provided in FIG. 2.

Primary study endpoints are the assessment of treatment-emergent adverse events, (TEAEs) serious treatment-emergent adverse events (TESAEs), clinical laboratory tests, and discontinuation of treatment for treatment-related TEAEs.

Secondary study endpoints are the proportion of subjects in whom R0 resection is achieved; surgical safety with respect to complication rates; FG-3019 plasma concentrations, including trough level ($C_{min}$) and $C_{max}$ (2 hour post end of infusion); tumor response rates as measured by CT scan per RECIST, serum CA19-9 (50% decrease from baseline), or FDG-PET (30% decrease in $SUV_{max}$ from baseline); overall survival and progression free survival.

Screening and Eligibility

This study is open to individuals at least 18 years old that have a histologically proven diagnosis of pancreatic ductal adenocarcinoma and measurable disease as defined by RECIST. Individuals must have laparoscopic confirmation that the PDAC is locally advanced. Additionally, individuals must have an Eastern Cooperative Oncology Group (ECOG) performance status (PS) 0 or 1. Further, individuals must have adequate liver function (aspartate aminotransferase (AST) and alanine aminotransferase (ALT)<2.5×upper limit of normal, alkaline phosphatase<2.5×upper limit of normal and bilirubin≤1.5×Upper Limit Normal (ULN)); adequate bone marrow function (platelets>100,000 cells/mm$^3$, hemoglobin>9.0 l/dL, and absolute neutrophil count (ANC)>1, 500 cells/mm$^3$); and adequate renal function (creatinine<1.5×ULN).

Induction Therapy

Eligible subjects are randomized 1:1 between Arms A and B to receive up to six cycles of induction therapy. Arm A consists of gemcitabine, 1000 mg/m$^2$ by IV infusion on days 1, 8 and 15 of each 28-day induction therapy cycle; Nab-paclitaxel, 125 mg/m$^2$ by IV infusion on days 1, 8 and 15 of each 28-day induction therapy cycle; and FG-3019, 35 mg/kg by IV infusion on days 1 and 15 of each 28-day induction therapy cycle. An extra dose of FG-3019 is given on Day 8 of the first induction therapy cycle as a loading dose.

Arm B consists of gemcitabine, 1000 mg/m$^2$ by IV infusion on days 1, 8 and 15 of each 28-day induction therapy cycle; and Nab-paclitaxel, 125 mg/m$^2$ by IV infusion on days 1, 8 and 15 of each 28-day induction therapy cycle.

Blood samples are collected periodically for the assessment of pharmacokinetics (PK) and pharmacodynamics (PD). All subjects are followed for 28 days after last cycle of induction therapy for safety endpoints.

Eligibility for Surgery

Subjects who complete six cycles of induction therapy undergo evaluation to determine their eligibility for surgery. To be eligible, subjects must achieve a reduction in CA19-9 level by more than 50% compared to a baseline CA19-9 measurement; a decrease by ≥30% of FDG-PET $SUV_{max}$ compared to a baseline measurement; or a partial response [PR] or complete response [CR] as per RECIST 1.1. Additionally, to be eligible, subjects must meet the definition of resectable or borderline resectable status.

Subjects are classified as ineligible if from a surgical perspective they have disease progression defined as any disease progression leading to SMV thrombosis or PV thrombosis; disease progression beyond 180 degrees on artery; or development of significant pancreatitis that makes surgery unsafe. Subjects are also ineligible if they develop distant metastases, exhibit clear local progression on CT scan or develop a new medical condition or the worsening of a pre-existing medical condition that makes surgery unsafe or is a contraindication to surgery.

Surgery

Eligible subjects undergo surgery with the intent to achieve R0 resection. If possible at the time of surgery, tumor tissue is obtained for analysis. If post-induction therapy tumor tissue cannot be safely obtained at the time of surgery, subjects are asked to undergo endoscopic ultrasound (EUS) and core biopsy. Subjects are followed for 30 days after discharge for assessment of post-operative complications.

Long-Term Follow Up

All subjects, including those who discontinue from the study during the induction therapy period without evidence of disease progression, are followed for up to 5 years until disease progression or survival.

Initial Results

Table 1 lists the initial tumor and cancer marker response seen in the first two patients of the clinical study following two cycles of induction therapy.

TABLE 1

Tumor Response Seen In Initial Patients Following Two Induction Therapy Cycles

|  | ARM A - Patient 1 Gemcitabine plus Nab-paclitaxel and FG-3019 | Arm B- Patient 1 Gemcitabine plus Nab-paclitaxel (Control Arm) |
| --- | --- | --- |
| Tumor regression per RECIST | 22% | 13% |
| CA19.9 reduction from baseline | 95.5% | 85.4% |

Various modifications of the invention, in addition to those shown and described herein, will become apparent to those skilled in the art from the foregoing description. Such modifications are intended to fall within the scope of the appended claims.

All references cited herein are hereby incorporated by reference herein in their entirety.

What is claimed is:

1. A method of treating locally advanced pancreatic cancer (LAPC) in a subject with unresectable locally advanced pancreatic cancer, the method comprising:

administering an anti-connective tissue growth factor (CTGF) antibody that is identical to the CLN-1 antibody produced by ATCC Accession No. PTA-6006 at a dose of at least about 35 mg/kg, gemcitabine at a dose of about 1000 mg/m$^2$, and nab-paclitaxel at a dose of about 125 mg/m$^2$;

restaging the subject by laparascopic examination; and if the LAPC is downstaged to resectable or borderline resectable status, then resecting the LAPC.

2. The method of claim 1, wherein the antibody is administered on days 1 and 15 and the gemcitabine and nab-paclitaxel are administered on days 1, 8 and 15 of a 28 day treatment cycle.

3. The method of claim 2 having up to six treatment cycles before restaging.

4. The method of claim 3, wherein a 35 mg/kg loading dose of the antibody is administered on day 8 of the first treatment cycle.

5. The method of claim 1, wherein the LAPC is an adenocarcinoma.

6. The method of claim 5, wherein the adenocarcinoma is ductal adenocarcinoma.

* * * * *